US010280227B2

(12) United States Patent
Adler et al.

(10) Patent No.: US 10,280,227 B2
(45) Date of Patent: May 7, 2019

(54) HIGHLY CONCENTRATED PHARMACEUTICAL FORMULATIONS

(71) Applicant: Genentech, Inc., South San Francisco, CA (US)

(72) Inventors: Michael Adler, Riehen (CH);
Hanns-Christian Mahler, Basel (CH);
Oliver Boris Stauch, Freiburg (DE)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/260,558

(22) Filed: Apr. 24, 2014

(65) Prior Publication Data

US 2015/0086537 A1    Mar. 26, 2015

Related U.S. Application Data

(63) Continuation of application No. 12/879,486, filed on Sep. 10, 2010, now abandoned.

(30) Foreign Application Priority Data

Sep. 11, 2009 (EP) .................................... 09170110

(51) Int. Cl.
| A61K 39/395 | (2006.01) |
| C07K 16/28 | (2006.01) |
| A61K 9/00 | (2006.01) |
| A61K 9/19 | (2006.01) |
| A61K 47/10 | (2017.01) |
| A61K 47/18 | (2017.01) |
| A61K 47/26 | (2006.01) |
| A61K 38/47 | (2006.01) |
| A61K 45/06 | (2006.01) |
| A61K 47/20 | (2006.01) |
| A61K 47/22 | (2006.01) |
| A61K 47/42 | (2017.01) |
| C07K 16/30 | (2006.01) |
| A61K 39/00 | (2006.01) |

(52) U.S. Cl.
CPC ........ *C07K 16/2887* (2013.01); *A61K 9/0019* (2013.01); *A61K 9/19* (2013.01); *A61K 38/47* (2013.01); *A61K 39/3955* (2013.01); *A61K 45/06* (2013.01); *A61K 47/10* (2013.01); *A61K 47/183* (2013.01); *A61K 47/20* (2013.01); *A61K 47/22* (2013.01); *A61K 47/26* (2013.01); *A61K 47/42* (2013.01); *C07K 16/3061* (2013.01); *A61K 2039/505* (2013.01); *C07K 2317/21* (2013.01); *C07K 2317/24* (2013.01); *C07K 2317/734* (2013.01); *C07K 2317/94* (2013.01)

(58) Field of Classification Search
None
See application file for complete search history.

(56) References Cited

U.S. PATENT DOCUMENTS

| 2,795,529 A | 6/1957 | Alburn et al. |
| 4,753,894 A | 6/1988 | Frankel et al. |
| 4,943,533 A | 7/1990 | Mendelsohn et al. |
| 5,500,362 A | 3/1996 | Robinson et al. |
| 5,558,864 A | 9/1996 | Bendig et al. |
| 5,677,171 A | 10/1997 | Hudziak et al. |
| 5,677,180 A | 10/1997 | Robinson et al. |
| 5,721,108 A | 2/1998 | Robinson et al. |
| 5,721,348 A | 2/1998 | Primakoff et al. |
| 5,736,137 A | 4/1998 | Anderson et al. |
| 5,776,456 A | 7/1998 | Anderson et al. |
| 5,783,186 A | 7/1998 | Arakawa et al. |
| 5,821,337 A | 10/1998 | Carter et al. |
| 5,843,439 A | 12/1998 | Anderson et al. |
| 5,891,996 A | 4/1999 | Mateo De Acosta Del Rio et al. |
| 6,120,767 A | 9/2000 | Robinson et al. |
| 6,127,526 A | 10/2000 | Blank |
| 6,171,586 B1 | 1/2001 | Lam et al. |
| 6,235,883 B1 | 5/2001 | Jakobovits et al. |
| 6,267,958 B1 | 7/2001 | Andya et al. |
| 6,333,398 B1 | 12/2001 | Blank |
| 6,399,061 B1 | 6/2002 | Anderson et al. |
| 6,417,335 B1 | 7/2002 | Basey et al. |
| 6,455,043 B1 | 9/2002 | Grillo-Lopez |
| 6,489,447 B1 | 12/2002 | Basey et al. |
| 6,506,883 B2 | 1/2003 | Meteo de Acosta del Rio et al. |
| 6,652,852 B1 | 11/2003 | Robinson et al. |
| 6,682,734 B1 | 1/2004 | Anderson et al. |

(Continued)

FOREIGN PATENT DOCUMENTS

| EP | 1331266 A1 | 7/2003 |
| EP | 1331266 A4 | 7/2003 |

(Continued)

OTHER PUBLICATIONS

PRNewswire, "Halozyme Therapeutics' Enhanze Technology . . . ", http:/twww.prnewswire.com/news-releases/halozyme-therapeutics-enhanze-technology-large-protein-molecue-therapeutic-clinical-trial-results-presented, Aug. 9, 2007, retrieved Oct. 26, 2016, pp. 1-3.*

(Continued)

*Primary Examiner* — Yunsoo Kim
(74) *Attorney, Agent, or Firm* — Wendy M. Lee

(57) ABSTRACT

The present invention relates to a highly concentrated, stable pharmaceutical formulation of a pharmaceutically active anti-CD20 antibody, such as e.g. Rituximab, Ocrelizumab, or HuMab<CD20>, or a mixture of such antibody molecules for subcutaneous injection. In particular, the present invention relates to formulations comprising, in addition to a suitable amount of the anti-CD20 antibody, an effective amount of at least one hyaluronidase enzyme as a combined formulation or for use in form of a co-formulation. The said formulations comprise additionally at least one buffering agent, such as e.g. a histidine buffer, a stabilizer or a mixture of two or more stabilizers (e.g. a saccharide, such as e.g. α,α-trehalose dihydrate or sucrose, and optionally methionine as a second stabilizer), a nonionic surfactant and an effective amount of at least one hyaluronidase enzyme. Methods for preparing such formulations and their uses thereof are also provided.

15 Claims, No Drawings

(56) References Cited

U.S. PATENT DOCUMENTS

| | | |
|---|---|---|
| 6,685,940 B2 | 2/2004 | Andya et al. |
| 6,797,814 B2 | 9/2004 | Blank |
| 6,821,515 B1 | 11/2004 | Cleland et al. |
| 6,846,476 B2 | 1/2005 | White |
| 6,875,432 B2 | 4/2005 | Liu et al. |
| 6,893,625 B1 | 5/2005 | Robinson et al. |
| 6,896,885 B2 | 5/2005 | Hanna |
| 6,991,790 B1 | 1/2006 | Lam et al. |
| 7,060,268 B2 | 6/2006 | Andya et al. |
| 7,381,560 B2 | 6/2008 | Anderson et al. |
| 7,422,739 B2 | 9/2008 | Anderson et al. |
| 7,517,670 B2 | 4/2009 | Umana et al. |
| 7,666,413 B2 | 2/2010 | Liu et al. |
| 7,682,609 B2 | 3/2010 | Andya et al. |
| 7,682,612 B1 | 3/2010 | White et al. |
| 7,744,877 B2 | 6/2010 | Anderson et al. |
| 7,767,429 B2 | 8/2010 | Bookbinder et al. |
| 7,829,081 B2 | 11/2010 | Bookbinder et al. |
| 7,846,431 B2 | 12/2010 | Bookbinder et al. |
| 7,871,607 B2 | 1/2011 | Bookbinder et al. |
| 8,105,586 B2 | 1/2012 | Bookbinder et al. |
| 8,142,776 B2 | 3/2012 | Liu et al. |
| 8,202,517 B2 | 6/2012 | Bookbinder et al. |
| 8,206,711 B2 | 6/2012 | White et al. |
| 8,257,699 B2 | 9/2012 | Bookbinder et al. |
| 8,329,172 B2 | 12/2012 | Grillo-Lopez |
| 8,372,396 B2 | 2/2013 | Andya et al. |
| 8,431,124 B2 | 4/2013 | Bookbinder et al. |
| 8,431,380 B2 | 4/2013 | Bookbinder et al. |
| 8,450,470 B2 | 5/2013 | Bookbinder et al. |
| 8,568,720 B2 | 10/2013 | Morichika et al. |
| 8,580,252 B2 | 11/2013 | Bookbinder et al. |
| 8,580,264 B2 | 11/2013 | Zhang et al. |
| 8,632,778 B2 | 1/2014 | Kakuta et al. |
| 8,703,126 B2 | 4/2014 | Liu et al. |
| 8,765,685 B2 | 7/2014 | Bookbinder et al. |
| 8,772,246 B2 | 7/2014 | Bookbinder et al. |
| 8,840,884 B2 | 9/2014 | Kakuta et al. |
| 8,921,527 B2 | 12/2014 | Mizushima et al. |
| 8,961,964 B2 | 2/2015 | Liu et al. |
| 9,017,671 B2 | 4/2015 | Andya et al. |
| 9,051,384 B2 | 6/2015 | Kakuta et al. |
| 9,084,777 B2 | 7/2015 | Morichika et al. |
| 9,180,189 B2 | 11/2015 | Andya et al. |
| 9,211,315 B2 | 12/2015 | Bookbinder et al. |
| 9,283,273 B2 | 3/2016 | Andya et al. |
| 9,296,821 B2 | 3/2016 | Grillo-Lopez |
| 9,345,661 B2 | 5/2016 | Adler et al. |
| 9,539,263 B2 | 1/2017 | Zhang et al. |
| 9,562,223 B2 | 2/2017 | Bookbinder et al. |
| 9,677,061 B2 | 6/2017 | Bookbinder et al. |
| 9,677,062 B2 | 6/2017 | Bookbinder et al. |
| 9,750,752 B2 | 9/2017 | Zhang et al. |
| 9,968,676 B2 | 5/2018 | Adler et al. |
| 10,016,491 B2 | 7/2018 | Bookbinder et al. |
| 10,034,940 B2 | 7/2018 | Liu et al. |
| 2001/0014326 A1 | 8/2001 | Andya et al. |
| 2001/0018041 A1 | 8/2001 | Hanna et al. |
| 2002/0006404 A1 | 1/2002 | Hanna et al. |
| 2002/0009444 A1 | 1/2002 | Grillo-Lopez |
| 2002/0012665 A1 | 1/2002 | Hanna |
| 2002/0028178 A1 | 3/2002 | Hanna et al. |
| 2002/0032317 A1 | 3/2002 | Blank |
| 2002/0035736 A1 | 3/2002 | Erickson et al. |
| 2002/0039557 A1 | 4/2002 | White |
| 2002/0045571 A1 | 4/2002 | Liu et al. |
| 2002/0058029 A1 | 5/2002 | Hanna |
| 2002/0128448 A1 | 9/2002 | Reff |
| 2002/0159996 A1 | 10/2002 | Hariharan et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026804 A1 | 2/2003 | Grillo-Lopez et al. |
| 2003/0082172 A1 | 5/2003 | Anderson et al. |
| 2003/0091561 A1 | 5/2003 | van de Winkel et al. |
| 2003/0095963 A1 | 5/2003 | Anderson et al. |
| 2003/0103971 A1 | 6/2003 | Hariharan et al. |
| 2003/0147885 A1 | 8/2003 | Anderson et al. |
| 2003/0157108 A1 | 8/2003 | Presta |
| 2003/0180290 A1 | 9/2003 | Hariharan et al. |
| 2003/0180292 A1 | 9/2003 | Hanna et al. |
| 2003/0190316 A1 | 10/2003 | Kakuta et al. |
| 2003/0202972 A1 | 10/2003 | Andya et al. |
| 2003/0206903 A1 | 11/2003 | Grillo-Lopez |
| 2003/0211107 A1 | 11/2003 | Hariharan et al. |
| 2004/0191256 A1 | 9/2004 | Raju |
| 2004/0197324 A1 | 10/2004 | Liu et al. |
| 2004/0202658 A1 | 10/2004 | Benyunes |
| 2004/0213784 A1 | 10/2004 | Grillo-Lopez et al. |
| 2004/0268425 A1 | 12/2004 | Bookbinder et al. |
| 2005/0032130 A1 | 2/2005 | Beresini et al. |
| 2005/0053602 A1 | 3/2005 | Brunetta |
| 2005/0095243 A1 | 5/2005 | Chan et al. |
| 2005/0112060 A1 | 5/2005 | White |
| 2005/0118163 A1 | 6/2005 | Mizushima et al. |
| 2005/0123540 A1 | 6/2005 | Hanna et al. |
| 2005/0123546 A1 | 6/2005 | Umana et al. |
| 2005/0158303 A1 | 7/2005 | Liu et al. |
| 2005/0158316 A1 | 7/2005 | Lam et al. |
| 2005/0163708 A1 | 7/2005 | Robinson et al. |
| 2005/0163775 A1 | 7/2005 | Chan et al. |
| 2005/0175603 A1 | 8/2005 | Liu et al. |
| 2005/0180975 A1 | 8/2005 | Hanna |
| 2005/0186205 A1 | 8/2005 | Anderson et al. |
| 2005/0186206 A1 | 8/2005 | Brunetta |
| 2005/0191297 A1 | 9/2005 | Brunetta |
| 2005/0214278 A1 | 9/2005 | Kakuta et al. |
| 2005/0255527 A1 | 11/2005 | Yang et al. |
| 2005/0260186 A1 | 11/2005 | Bookbinder et al. |
| 2005/0271658 A1 | 12/2005 | Brunetta et al. |
| 2005/0276803 A1 | 12/2005 | Chan et al. |
| 2006/0002930 A1 | 1/2006 | Brunetta et al. |
| 2006/0024295 A1 | 2/2006 | Brunetta |
| 2006/0024300 A1 | 2/2006 | Adams et al. |
| 2006/0034835 A1 | 2/2006 | Adams et al. |
| 2006/0051345 A1 | 3/2006 | Frohna |
| 2006/0062787 A1 | 3/2006 | Hitraya |
| 2006/0067930 A1 | 3/2006 | Adams et al. |
| 2006/0088523 A1 | 4/2006 | Andya et al. |
| 2006/0099201 A1 | 5/2006 | Andya et al. |
| 2006/0099662 A1 | 5/2006 | Chuntharapai et al. |
| 2006/0104968 A1 | 5/2006 | Bookbinder et al. |
| 2006/0110387 A1 | 5/2006 | Brunetta |
| 2006/0121028 A1 | 6/2006 | Reff |
| 2006/0134111 A1 | 6/2006 | Agarwal |
| 2006/0135430 A1 | 6/2006 | Chan et al. |
| 2006/0171950 A1 | 8/2006 | Hariharan et al. |
| 2006/0172385 A1 | 8/2006 | Ernst et al. |
| 2006/0179501 A1 | 8/2006 | Chan et al. |
| 2006/0182739 A1 | 8/2006 | Basey et al. |
| 2006/0188495 A1 | 8/2006 | Barron et al. |
| 2006/0218655 A1 | 9/2006 | Chan et al. |
| 2006/0233797 A1 | 10/2006 | Gujrathi |
| 2006/0240007 A1 | 10/2006 | Sanders |
| 2006/0240008 A1 | 10/2006 | Benyunes |
| 2006/0246004 A1 | 11/2006 | Adams et al. |
| 2006/0263349 A1 | 11/2006 | Mccutcheon et al. |
| 2006/0263355 A1 | 11/2006 | Quan et al. |
| 2006/0275284 A1 | 12/2006 | Hanna |
| 2006/0286100 A1 | 12/2006 | Hariharan et al. |
| 2006/0286101 A1 | 12/2006 | Hariharan et al. |
| 2007/0003544 A1 | 1/2007 | Hanna |
| 2007/0009518 A1 | 1/2007 | Novobrantseva et al. |
| 2007/0009519 A1 | 1/2007 | Hariharan et al. |
| 2007/0020260 A1 | 1/2007 | Presta |
| 2007/0020261 A1 | 1/2007 | Sliwkowski et al. |
| 2007/0025987 A1 | 2/2007 | Brunetta |
| 2007/0031331 A1 | 2/2007 | Brunetta et al. |
| 2007/0053900 A1 | 3/2007 | Liu et al. |
| 2007/0071675 A1 | 3/2007 | Wu et al. |
| 2007/0086995 A1 | 4/2007 | Liu et al. |
| 2007/0116700 A1 | 5/2007 | Liu et al. |
| 2007/0212733 A1 | 9/2007 | Martin |
| 2007/0231324 A1 | 10/2007 | Ashkenazi |

(56) References Cited

U.S. PATENT DOCUMENTS

| | | |
|---|---|---|
| 2008/0038261 A1 | 2/2008 | Grillo-Lopez |
| 2008/0044421 A1 | 2/2008 | Ashkenazi |
| 2008/0075719 A1 | 3/2008 | Chan et al. |
| 2008/0089893 A9 | 4/2008 | Anderson et al. |
| 2008/0095771 A1 | 4/2008 | Barron et al. |
| 2008/0176257 A9 | 7/2008 | Chuntharapai et al. |
| 2008/0213280 A1 | 9/2008 | Benyunes |
| 2008/0306247 A1 | 12/2008 | Mizushima et al. |
| 2009/0004189 A1 | 1/2009 | Behrens et al. |
| 2009/0010921 A1 | 1/2009 | Umana et al. |
| 2009/0053786 A1 | 2/2009 | Kao et al. |
| 2009/0060913 A1 | 3/2009 | Friess et al. |
| 2009/0098118 A1 | 4/2009 | Friess et al. |
| 2009/0110688 A1 | 4/2009 | Fertig et al. |
| 2009/0123367 A1 | 5/2009 | Bookbinder et al. |
| 2009/0131639 A1 | 5/2009 | Kakuta et al. |
| 2009/0148435 A1 | 6/2009 | Lebreton et al. |
| 2009/0155257 A1 | 6/2009 | Adams et al. |
| 2009/0162352 A1 | 6/2009 | Adler et al. |
| 2009/0169550 A1 | 7/2009 | Dummer |
| 2009/0175854 A1 | 7/2009 | Ashkenazi |
| 2009/0181013 A1 | 7/2009 | Bookbinder et al. |
| 2009/0181032 A1 | 7/2009 | Bookbinder et al. |
| 2009/0196879 A1 | 8/2009 | Mella et al. |
| 2009/0202473 A1 | 8/2009 | Neri et al. |
| 2009/0214505 A1 | 8/2009 | Bookbinder et al. |
| 2009/0214561 A1 | 8/2009 | Close |
| 2009/0246197 A1 | 10/2009 | Dumontet et al. |
| 2009/0253175 A1 | 10/2009 | Bookbinder et al. |
| 2009/0269339 A1 | 10/2009 | Kelman et al. |
| 2009/0280129 A1 | 11/2009 | Liu et al. |
| 2009/0291076 A1 | 11/2009 | Morichika et al. |
| 2009/0311255 A1 | 12/2009 | Brunetta et al. |
| 2009/0317384 A1 | 12/2009 | Ashkenazi |
| 2010/0015157 A1 | 1/2010 | Andya et al. |
| 2010/0158898 A1 | 6/2010 | Liu et al. |
| 2010/0158899 A1 | 6/2010 | Andya et al. |
| 2010/0158903 A1 | 6/2010 | Smith et al. |
| 2010/0196423 A1 | 8/2010 | Bookbinder et al. |
| 2010/0211015 A1 | 8/2010 | Bookbinder et al. |
| 2010/0285011 A1 | 11/2010 | Morichika et al. |
| 2011/0008309 A1 | 1/2011 | Bookbinder et al. |
| 2011/0044977 A1 | 2/2011 | Adler et al. |
| 2011/0076273 A1 | 3/2011 | Adler et al. |
| 2011/0152359 A1 | 6/2011 | Bookbinder et al. |
| 2011/0236383 A1 | 9/2011 | Andya et al. |
| 2012/0064086 A1 | 3/2012 | Liu et al. |
| 2012/0076783 A1 | 3/2012 | Liu et al. |
| 2012/0093770 A1 | 4/2012 | Bookbinder et al. |
| 2012/0148555 A1 | 6/2012 | Bookbinder et al. |
| 2012/0251534 A1 | 10/2012 | Grillo-Lopez |
| 2012/0251535 A1 | 10/2012 | Grillo-Lopez |
| 2012/0251620 A1 | 10/2012 | Bookbinder et al. |
| 2012/0258101 A1 | 10/2012 | Grillo-Lopez |
| 2012/0258102 A1 | 10/2012 | Grillo-Lopez |
| 2012/0294830 A1 | 11/2012 | Bookbinder et al. |
| 2012/0301460 A1 | 11/2012 | Bao et al. |
| 2013/0058893 A1 | 3/2013 | Bookbinder et al. |
| 2013/0071384 A1 | 3/2013 | Andya et al. |
| 2013/0216532 A1 | 8/2013 | Adler et al. |
| 2013/0224185 A1 | 8/2013 | Andya et al. |
| 2013/0236448 A1 | 9/2013 | Kamerzell et al. |
| 2013/0273039 A1 | 10/2013 | Grillo-Lopez |
| 2014/0005367 A1 | 1/2014 | Morichika et al. |
| 2014/0037613 A1 | 2/2014 | Bookbinder et al. |
| 2014/0056883 A1 | 2/2014 | Zhang et al. |
| 2014/0056884 A1 | 2/2014 | Zhang et al. |
| 2014/0056885 A1 | 2/2014 | Zhang et al. |
| 2014/0056887 A1 | 2/2014 | Grillo-Lopez |
| 2014/0199282 A1 | 7/2014 | Bookbinder et al. |
| 2014/0248237 A1 | 9/2014 | Bookbinder et al. |
| 2015/0044198 A1 | 2/2015 | Liu et al. |
| 2015/0086537 A1 | 3/2015 | Adler et al. |
| 2015/0165059 A1 | 6/2015 | Bookbinder et al. |
| 2015/0183882 A1 | 7/2015 | Grillo-Lopez |
| 2015/0196623 A9 | 7/2015 | Bookbinder et al. |
| 2015/0196642 A1 | 7/2015 | Andya et al. |
| 2015/0225485 A1 | 8/2015 | Liu et al. |
| 2015/0284466 A1 | 10/2015 | Morichika et al. |
| 2016/0051640 A1 | 2/2016 | Bookbinder et al. |
| 2016/0090419 A1 | 3/2016 | Morichika et al. |
| 2016/0137742 A1 | 5/2016 | Adler et al. |
| 2016/0166689 A1 | 6/2016 | Adler et al. |
| 2016/0333106 A1 | 11/2016 | Grillo-Lopez |
| 2016/0367675 A1 | 12/2016 | Liu et al. |
| 2017/0037140 A1 | 2/2017 | Grillo-Lopez |
| 2017/0049888 A1 | 2/2017 | Liu et al. |
| 2017/0360807 A1 | 12/2017 | Zhang et al. |
| 2018/0221488 A1 | 8/2018 | Andya et al. |
| 2018/0228895 A1 | 8/2018 | Adler et al. |

FOREIGN PATENT DOCUMENTS

| | | |
|---|---|---|
| EP | 0590058 B1 | 11/2003 |
| EP | 1603541 B1 | 11/2009 |
| EP | 2459167 B1 | 5/2013 |
| EP | 1516628 B1 | 8/2013 |
| WO | 93/21319 A1 | 10/1993 |
| WO | 94/00136 A1 | 1/1994 |
| WO | 94/11026 A2 | 5/1994 |
| WO | 94/11026 A3 | 5/1994 |
| WO | 94/11026 R1 | 5/1994 |
| WO | 95/20045 A1 | 7/1995 |
| WO | 96/40210 A1 | 12/1996 |
| WO | 97/04801 | 2/1997 |
| WO | 97/04801 A1 | 2/1997 |
| WO | 98/22136 A2 | 5/1998 |
| WO | 99/57134 A1 | 11/1999 |
| WO | 01/00245 A2 | 1/2001 |
| WO | 01/00245 A3 | 1/2001 |
| WO | 01/62931 A2 | 8/2001 |
| WO | 01/62931 A3 | 8/2001 |
| WO | 01/88138 A1 | 11/2001 |
| WO | 2004/056312 A2 | 7/2004 |
| WO | 2004/078140 A2 | 9/2004 |
| WO | 2004/110498 A2 | 12/2004 |
| WO | 2005/023328 A2 | 3/2005 |
| WO | 2005/037992 A2 | 4/2005 |
| WO | 2005/044859 A2 | 5/2005 |
| WO | 2005/044859 A3 | 5/2005 |
| WO | 2005/117986 A2 | 12/2005 |
| WO | 2006/033700 A2 | 3/2006 |
| WO | 2006/044908 A2 | 4/2006 |
| WO | 2006/081587 A2 | 8/2006 |
| WO | 2006/084264 A2 | 8/2006 |
| WO | 2006/091871 A1 | 8/2006 |
| WO | 2007/005608 A2 | 1/2007 |
| WO | 2007/019899 A2 | 2/2007 |
| WO | 2007/024715 A2 | 3/2007 |
| WO | 2007/024715 A3 | 3/2007 |
| WO | 2007/024715 A9 | 3/2007 |
| WO | 2007/031875 A2 | 3/2007 |
| WO | 2007/076062 A2 | 7/2007 |
| WO | 2007/109221 A2 | 9/2007 |
| WO | 2007/109221 A3 | 9/2007 |
| WO | 2007/110339 A1 | 10/2007 |
| WO | 2008/150949 A1 | 12/2008 |
| WO | 2008/063776 A2 | 3/2009 |
| WO | 2008/063776 A3 | 3/2009 |
| WO | 2009/049841 A1 | 4/2009 |
| WO | 2009/055343 A2 | 4/2009 |
| WO | 2009/080541 A1 | 7/2009 |
| WO | 2010/029054 A1 | 3/2010 |
| WO | 2010/031720 A2 | 3/2010 |
| WO | 2010/031720 A3 | 3/2010 |
| WO | 2011/012637 A2 | 2/2011 |
| WO | 2011/012637 A3 | 2/2011 |
| WO | 2011/012637 A4 | 2/2011 |

OTHER PUBLICATIONS

Halozyme Therapeutics, "Matrix Therapies for Life", https:/lwww.sec.gov/Archives/edgar/data/1159036l000095012309014541/

(56) References Cited

OTHER PUBLICATIONS a52925exvW.V1.htm, Jun. 17, 2009, retrieved Oct. 26, 2016, pp. 1-30.*
NHS, "BP22333 Phase 1b Rituximab SC as Maintenance Treatment in fNHL (FL)", Sep. 9, 2009, pp. 1-2, http://www.hra.nhs.uk/news/research-summaries/bp22333-phase-1b-rituximab-sc-as-maintenance-treatment-in-fnhl-fl/, retrieved Jun. 8, 2017.*
Mack, G., "CD20 blockers eye crowded rheumatology market" Nature Biotechnology 26(10):1053-1054 (Oct. 2008).
Declaration of Prof. Dr. Wolfgang Friess Under 37 C.F.R. 1.132 dated Jun. 11, 2015 with Exhibits A-F (filed in Adler et al., U.S. Appl. No. 12/804,703, filed Jul. 27, 2010, Subcutaneous Anti-HER2 Antibody Formulations and Uses Thereof) pp. 1-89 (Jun. 11, 2015).
Baxter, "Hylenex recombinant (hyaluronidase human injection)" (Prescribing Information),:1-2 (Oct. 2008).
Carpenter et al., "Inhibition of stress-induced aggregation of protein therapeutics" Methods in Enzymology 309:236-255 ( 1999).
Chi et al., "Physical stability of proteins in aqueous solution: mechanism and driving forces in nonnative protein aggregation" Pharm Res 20(9):1325-1336 (Sep. 2003).
F. Hoffmann-La Roche AG, (International Appln. No. PCT/EP2010/060930, International Filing Date Jul. 28, 2010; Certified Priority Document EP 09167025.7/EP 0916705, filed Jul. 31, 2009 from Adler et al., EP Appln. 10737891.1, filed Jul. 28, 2010; EP 2,459,167 Opposition; *HGF Limited v. F. Hoffmann-La Roche AG*),:1-57 (Jul. 31, 2009).
Frieβ, W., "Declaration of Prof. Dr. Wolfgang Frieβ" (Adler et al., EP Appln. 10737891.1, filed Jul. 28, 2010; EP 2,459,167 Opposition; *HGF Limited v. F. Hoffmann-La Roche AG*),:1-11, Annex A&B, Ex. 1-5 (Aug. 7, 2015).
Frost, G. I. et al., "A microtiter-based assay for hyaluronidase activity not requiring specialized reagents" Anal Biochem 251(2):263-9 (Sep. 1997).
Galush et al., "Viscosity Behavior of High-Concentration Protein Mixtures" Journal of Pharmaceutical Sciences 101(3):1012-1020 (2012).
Ismael et al., "Subcutaneous versus intravenous administration of (neo)adjuvant trastuzumab in patients with HER2-positive, clinical stage I-III breast cancer (HannaH study): a phase 3, open-label, multicentre, randomised trial" Lancet Oncol 13(9):869-878 (Sep. 2012).
Jones, A. J. S., "Analysis of Polypeptides and Proteins." Adv Drug Delivery Rev 10:29-90 ( 1993).
Krishnan et al. Formulation and Process Development Strategies for Manufacturing Biopharmaceuticals "Chapter 16: Development of Formulations for Therapeutic Monoclonal Antibodies and Fc Fusion Proteins" Jameel and Hershenson, John Wiley & Sons, Inc., 383-427 (2010).
Melamed et al., "Recombinant Human Hyaluronidase Facilitates Dispersion of Subcutaneously Administered Gammagard Liquid and Enables Administration of a Full Monthly Dose in a Single Site to Patients with Immunodeficiency Diseases" Journal of Allergy and Clinical Immunology 121(2 Suppl 1):S83 (Feb. 2008)
Pearlman, R. et al. Peptide and Protein Drug Delivery "Chapter 6, Analysis of Protein Drugs" Vincent H. L. Lee, Marcel Dekker, Inc., 247-301 (1991).
Pivot et al., "Preference for subcutaneous or intravenous administration of trastuzumab in patients with HER2-positive early breast cancer (PrefHer): an open-label randomised study" Lancet Oncol 14:962-970 ( 2013).
Ratner, M., "Roche plans for more convenient-to-use Herceptin and Rituxan" Nature Biotechnology 28(4):298 (Apr. 2010).
Shpilberg et al., "Subcutaneous administration of rituximab (MabThera) and trastuzumab (Herceptin) using hyaluronidase" British Journal of Cancer 109(6):1556-1561 (Sep. 17, 2013).
Davies et al., "Pharmacokinetics (PK), safety and overall response rate (ORR) achieved with subcutaneous (SC) administration of rituximab in combination with chemotherapy were comparable to those achieved with intravenous (IV) administration in patients (pts) with follicular lymphoma (FL) in the first-line setting: stage 1 results of the phase III SABRINA study (BO22334)" Blood (Abstract 1629; retrieved Oct. 6, 2016), 120:1629 ( 2012).
Davies et al., "Pharmacokinetics and safety of subcutaneous rituximab in follicular lymphoma (SABRINA): stage 1 analysis of a randomised phase 3 study" Lancet Oncol 15(3):343-352 (Mar. 2014).
De Cock et al., "Time Savings with Rituximab Subcutaneous Injection versus Rituximab Intravenous Infusion: A Time and Motion Study in Eight Countries" PLoS One 11(6):e0157957; pp. 1-16 (Jun. 30, 2016)
Forstpointner et al., "Maintenance therapy with rituximab leads to a significant prolongation of response duration after salvage therapy with a combination of rituximab, fludarabine, cyclophosphamide, and mitoxantrone (R-FCM) in patients with recurring and refractory follicular and mantle cell lymphomas: Results of a prospective randomized study of the German Low Grade Lymphoma Study Group (GLSG)" Blood 108(13):4003-4008 (Dec. 15, 2006).
Friess, W., "Declaration of Professor Wolfgang Friess under 37 C.F.R. 1.132" (Filed in Adler et al., U.S. Appl. No. 14/260,558, filed Apr. 24, 2014, Highly Concentrated Pharmaceutical Formulations),:1-8 with Exhibit A consisting of CV and list of publications pp. 9-20 (Sep. 10, 2016).
Ghielmini et al., "Prolonged treatment with rituximab in patients with follicular lymphoma significantly increases event-free survival and response duration compared with the standard weekly x 4 schedule" Blood 103(12):4416-4423 (Jun. 15, 2004).
Halozyme Therapeutics, Inc., "FDA accepts Genentech's biologics license application for subcutaneous formulation of rituximab" (press release; retrieved Jan. 31, 2017),:1-3 (Nov. 3, 2016) http://www.halozyme.com/investors/news-releases/news-release-details/2016/FDA-Accepts-Genentechs-Biologics-License-Application-For-Subcutaneous-Formulation-Of-Rituximab/default.aspx.
Harb et al., "Safety and pharmacokinetics of subcutaneous ceftriaxone administered with or without recombinant human hyaluronidase (rHuPH20) versus intravenous ceftriaxone administration in adult volunteers" Current Medical Research & Opinion 26(2):279-288 (Feb. 2010).
Hochster et al., "Maintenance rituximab after cyclophosphamide, vincristine, and prednisone prolongs progression-free survival in advanced indolent lymphoma: results of the randomized phase III ECOG1496 Study" Journal of Clinical Oncology 27(10):1607-1614 (Apr. 1, 2009).
Keating et al., "High-dose rituximab therapy in chronic lymphocytic leukemia" Seminars in Oncology 6(Suppl 12):86-90 (Dec. 2000).
Moreau et al., "Prospective comparison of subcutaneous versus intravenous administration of bortezomib in patients with multiple myeloma" Haematologica 93(12):1908-1911 (Dec. 2008).
Moreau et al., "Subcutaneous versus intravenous administration of bortezomib in patients with relapsed multiple myeloma: a randomised, phase 3, non-inferiority study" Lancet Oncol 12:431-440 (May 2011).
O'Brien et al., "Rituximab dose-escalation trial in chronic lymphocytic leukemia" J Clin Oncol. 19(8):2165-2170 (Apr. 15, 2001).
Sacco et al., "The average body surface area of adult cancer patients in the UK: a multicentre retrospective study." PLoS One (doi: 10.1371/journal.pone.0008933), 5(1):e8933 (pp. 1-6) (Jan. 28, 2010).
Salar et al., "A Two-Stage Phase Ib Study to Investigate the Pharmacokinetics, Safety and Tolerability of Subcutaneous Rituximab in Patients with Follicular Lymphoma as Part of Maintenance Treatment" Blood (Abstract 2858; retrieved Mar. 10, 2016), 116(21):1-2 (Nov. 19, 2010) http://www.bloodjournal.org/content/116/21/2858.
Salar et al., "Comparison of subcutaneous versus intravenous administration of rituximab as maintenance treatment for follicular lymphoma: results from a two-stage, phase IB study" Journal of Clinical Oncology (doi: 10.1200/JCO.2013.52.2631), 32(17):1782-1791 (Jul. 10, 2014).
Stilgenbauer et al., "Subcutaneous alemtuzumab in fludarabine-refractory chronic lymphocytic leukemia: clinical results and prognostic marker analyses from the CLL2H study of the German Chronic Lymphocytic Leukemia Study Group" Journal of Clinical Oncology 27(24):3994-4001 (Aug. 20, 2009).
Taylor, P., "AbbVie drops Halozyme formulation of blockbuster Humira after disappointing trial" FierceBiotech (retrieved Jan. 31,

(56) References Cited

OTHER PUBLICATIONS

2017),:1-2 (Nov. 22, 2016) http://www.fiercebiotech.com/biotech/abbvie-drops-halozyme-formulation-blockbuster-humira-after-disappointing-trial.

Thomas et al., "The INFUSE-Morphine study: use of recombinant human hyaluronidase (rHuPH20) to enhance the absorption of subcutaneously administered morphine in patients with advanced illness" Journal of Pain and Symptom Management 38(5):663-672 (Nov. 2009).

van Oers et al., "Rituximab maintenance improves clinical outcome of relapsed/resistant follicular non-Hodgkin lymphoma in patients both with and without rituximab during induction: results of a prospective randomized phase 3 intergroup trial" Blood 108(10):3295-3301 (Nov. 15, 2006).

van Oers et al., "Rituximab maintenance treatment of relapsed/resistant follicular non-Hodgkin's lymphoma: long-term outcome of the EORTC 20981 phase III randomized intergroup study" Journal of Clinical Oncology 28(17):2853-2858 (Jun. 10, 2010).

Yocum et al., "Clinical trial of recombinant human PH20 hyaluronidase's effect on subcutaneous absorption and pharmacokinetics of a large protein molecule therapeutic" (Proceedings of the 34th Annual Meeting and Exposition of the Controlled Release Society held Jul. 7-11, 2007, Long Beach, California),:1-2 (2007).

Arming, S. et al., "In vitro Mutagenesis of PH-20 Hyaluronidase from Human Sperm" Eur J Biochem 247:810-814 (1997).

Aukland, K. et al., "Interstitial-Lymphatic Mechanisms in the Control of Extracellular Fluid Volume" Physiology Reviews 73:1-78 (1993).

Baxter, "Hylenex recombinant (hyaluronidase human injection) 150 USP units/mL" (Prescribing Information) pp. 1-3 (2009).

Bertrand, P. et al., "Hyaluronan (Hyaluronic Acid) and Hyaluronectin in the Extracellular Matrix of Human Breast Carcinomas: Comparison Between Invasive and Non-Invasive Areas" Int J Cancer 52:1-6 (1992).

Bookbinder et al. et al., "A Recombinant Human Enzyme for Enhanced Interstitial Transport of Therapeutics" Journal of Controlled Release 114:230-241 ( 2006).

Bywaters, E. G. L. et al., "Reconstitution of the Dermal Barrier to Dye Spread After Hyaluronidase Injection" Brit Med J 2(4741):1178-1183 (Nov. 1951).

Chain, E., "A Mucolytic Enzyme in Testes Extracts" Nature 144:977-978 (1939).

Cherr, G. N. et al., "The PH-20 Protein in Cynomolgus Macaque Spermatozoa: Identification of Two Different Forms Exhibiting Hyaluronidase Activity" Dev Biol 175:142-153 (1996).

Cragg et al., "Antibody specificity controls in vivo effector mechanisms of anti-CD20 reagents" Blood 103(7):2738-2743 ( 2004).

Cragg et al., "Complement-mediated lysis by anti-CD20 mAb correlates with segregation into lipid rafts" Blood 101(3):1045-1052 (Feb. 1, 2003).

Danilkovitch-Miagkova, A. et al., "Hyaluronidase 2 Negatively Regulates RON Receptor Tyrosine Kinase and Mediates Transformation of Epithelial Cells by Jaagsiekte Sheep Retrovirus" P Natl Acad Sci USA 100(8):4580-4585 (Apr. 15, 2003).

Duran-Reynals, F., "A Spreading Factor in Certain Snake Venoms and Its Relation to Their Mode of Action" CR Soc. Biol. Paris pp. 69-81 (1938).

Frost, G. I. et al., "Purification, Cloning, and Expression of Human Plasma Hyaluronidase" Biochem Bioph Res Co 236:10-15 (1997).

Frost, Gregory I., "Recombinant Human Hyaluronidase (rHuPH20): an Enabling Platform for Subcutaneous Drug and Fluid Administration" Expert Opin Drug Del 4(4):427-440 (2007).

Harris et al., "Endocytic Function, Glycosaminoglycan Specificity, and Antibody Sensitivity of the Recombinant Human 190-kDa Hyaluronan Receptor for Endocytosis (HARE)" The Journal of Biological Chemistry 279(35):36201-36209 (2004).

Kiese, S. et al., "Shaken, Not Stirred: Mechanical Stress Testing of an IgG1 Antibody" J Pharm Sci 97(10):4347-4366 (Oct. 2008).

Kimata, K. et al., "Increased Synthesis of Hyaluronic Acid by Mouse Mammary Carcinoma Cell Variants with High Metastatic Potential" Cancer Res 43:1347-1354 (Mar. 1983).

Knudson, C. B. et al., "Hyaluronan-binding proteins in development, tissue homeostasis, and disease" FASEB J 7:1233-1241 (Oct. 1993).

Lalancette, C. et al., "Characterization of an 80-Kilodalton Bull Sperm Protein Identified as PH-20" Biology of Reproduction 65:628-636 (2001).

Laurent et al. Degradation of Bioactive Substances: Physiology and Pathophysiology, J.H. Henriksen, Boca Raton, FL:CRC Press pp. 249-265 (1991).

Laurent, T. C. et al., "Hyaluronan" FASEB J 6:2397-2404 (Apr. 1992).

Laurent, U. B. G. et al., "Catabolism of Hyaluronan in Rabbit Skin Takes Place Locally, In Lymph Nodes and Liver" Exp Physiol 76:695-703 ( 1991).

Ozzello, L. et al., "Growth-promoting Activity of Acid Mucopolysaccharides on a Strain of Human Mammary Carcinoma Cells" Cancer Res 20:600-604 (Jun. 1960).

Phelps, B. M. et al., "Restricted Lateral Diffusion of PH-20, a PI-Anchored Sperm Membrane Protein" Science 240:1780-1782 (Jun. 1988).

Pirrello et al., "Initial experiences with subcutaneous recombinant human hyaluronidase" J Palliat Med 10(4):861-4 (Aug. 2007).

Roskos, L. K. et al., "The clinical pharmacology of therapeutic monoclonal antibodies" Drug Develop Res 61(3):108-120 ( 2004).

Shire, S. J. et al., "Challenges in the Development of High Protein Concentration Formulations" J Pharm Sci 93(6):1390-1402 (Jun. 2004).

Supersaxo, A. et al., "Effect of Molecular Weight on the Lymphatic Absorption of Water-Soluble Compounds Following Subcutaneous Administration" Pharm Res. 7(2):167-169 ( 1990).

Swartz, Melody A., "The Physiology of the Lymphatic System" Adv Drug Deliver Rev 50:3-20 ( 2001).

Takeuchi, J. et al., "Variation in Glycosaminoglycan Components of Breast Tumors" Cancer Res 36:2133-2139 (Jul. 1976).

Tammi et al., "Degradation of Newly Synthesized High Molecular Mass Hyaluronan in the Epidermal and Dermal Compartments of Human Skin in Organ Culture" J. Invest. Dermatol 97:126-130 (1991).

Toole, Bryan P. Cell Biology of Extracellular Matrix "9" Elizabeth D. Hay, 2nd edition, New York:Plenum Press,:305-341 ( 1991).

Weissmann, Bernard, "The Transglycosylative Action of Testicular Hyaluronidase" J Biol Chem 216:783-794 ( 1955).

Aue et al., "Fractionated subcutaneous rituximab is well-tolerated and preserves CD20 expression on tumor cells in patients with chronic lymphocytic leukemia" Haematologica 95(2):329-332 ( 2010).

Gehan et al., "Estimation of human body surface area from height and weight" Cancer Chemotherapy Reports Part 1 vol. 54(4):225-235 (Aug. 1970).

Khouri et al., "Concurrent Administration of High-Dose Rituximab Before and After Autologous Stem-Cell Transplantation for Relapsed Aggressive B-Cell Non-Hodgkin's Lymphomas" Journal of Clinical Oncology 23(10):2240-2247 ( 2005).

Rituximab and hyaluronidase human injection, for subcutaneous use ("Rituximab SC") United States Prescribing Information., pp. 1-30 (2018).

Yang et al., "Crystalline monoclonal antibodies for subcutaneous delivery" P Natl Acad Sci USA 100(12):6934-9 (Jun. 2003).

Adler, M., "Declaration of Dr. Michael Adler" (Adler et al., EP Appln. 10737891.1, filed Jul. 28, 2010; EP 2,459,167 Opposition; *HGF Limited* v. *F. Hoffmann-La Roche AG* (signed by Dr. Adler Aug. 17, 2015 and submitted to European Patent Office on Aug. 19, 2015)),:1-10 (Annex A: Adler's C.V. included).

Andersen et al., "Aggregation of a multidomain protein: A coagulation mechanism governs aggregation of a model IgG1 antibody under weak thermal stress" Protein Science 19:279-290 ( 2010).

CAS Registry No. 757971-58-7 Hylenex Protein Sequence/36-482-Hyaluronoglucosaminidase PH20 (human) (Sequence published Oct. 7, 2004. Retrieved Sep. 8, 2016), pp. 1.

(56) References Cited

OTHER PUBLICATIONS

ClinicalTrials.gov, "A pharmacokinetic study of subcutaneous and intravenous rituximab in participants with follicular lymphoma" (NCT00930514 on Sep. 1, 2016; retrieved Sep. 9, 2016),:1-3 https://clinicaltrials.gov/archive/NCT00930514/2016_09_01.

ClinicalTrials.gov, "A pharmacokinetic study of subcutaneous and intravenous MabThera (rituximab) in patients with follicular lymphoma" (NCT00930514 on Aug. 17, 2010; retrieved Sep. 9, 2016),:1-3 https://clinicaltrials.gov/archive/NCT00930514/2010_08_17.

ClinicalTrials.gov, "A pharmacokinetic study of subcutaneous and intravenous MabThera (rituximab) in patients with follicular lymphoma" (NCT00930514 on Aug. 18, 2009; retrieved Jul. 11, 2016),:1-3 https://clinicaltrials.gov/archive/NCT00930514/2009_08_18.

Friess et al., "Bone Regeneration with Recombinant Human Bone Morphogenetic Protein-2 (rhBMP-2) Using Absorbable Collagen Sponges (ACS): Influence of Processing on ACS Characteristics and Formulation" Pharmaceutical Development and Technology 4(3):387-396 ( 1999).

Hawe et al., "Stabilization of a Hydrophobic Recombinant Cytokine by Human Serum Albumin" Journal of Pharmaceutical Sciences 96(11):2987-2999 (Nov. 2007).

Moorhouse et al., "Validation of an HPLC method for the analysis of the charge heterogeneity of the recombinant monoclonal antibody IDEC-C2B8 after papain digestion" J Pharmaceutical Biomedical Analysis 16(4):593-603 (Dec. 1997).

Morrow et al., "Addition of Human Hyaluronidase to Rapid Analog Insulin Reduces the Absolute Variability of Early Insulin Absorption across Infusion Set Life" (Poster 27-LB and Abstract 27-LB) American Diabetes Association (ADA) 71st Scientific Sessions, Jun. 24-28, 2011, pp. LB8 (2011).

Rituximab United States Prescribing Information (USPI),:1-31 ( 2009).

Rituximab, accession No. DB00073 (BTD00014, BIOD00014) (DrugBank: Drug created Jun. 13, 2005; Updated Aug. 17, 2016; Retrieved Aug. 25, 2016),:1-9 http://www.drugbank.ca/drugs/DB00073.

Wyeth, ReFacto® (Antihemophilic Factor, Recombinant) prescribing information, (revised Dec. 2007),:1-18.

Wynne et al., "Comparison of Subcutaneous and Intravenous Administration of Trastuzumab: A Phase I/Ib Trial in Healthy Male Volunteers and Patients with HER2-Positive Breast Cancer" The Journal of Clinical Pharmacology (Published online Feb. 22, 2012; DOI: 10.1177/0091270012436560), 53(2):192-201 ( 2013).

U.S. Appl. No. 15/253,571, filed Aug. 31, 2016.

U.S. Appl. No. 15/253,689, filed Aug. 31, 2016.

\* cited by examiner

HIGHLY CONCENTRATED PHARMACEUTICAL FORMULATIONS

This is a continuation application which claims priority under 35 USC § 120 to non-provisional application Ser. No. 12/879,486, filed Sep. 10, 2010, which claims priority under 35 USC § 119 to European Patent Application No. 09170110.2, filed Sep. 11, 2009, the contents of which are incorporated herein by reference.

The present invention relates to highly concentrated, stable pharmaceutical formulations of a pharmaceutically active anti-CD20 antibody or a mixture of such antibody molecules for subcutaneous injection. Such formulations comprise, in addition to the high amounts of anti-CD20 antibody or mixture thereof, a buffering agent, a stabilizer or a mixture of two ore more stabilizing agents, a nonionic surfactant and an effective amount of at least one hyaluronidase enzyme. The invention also relates to a process for the preparation of the formulation and to the uses of such formulation.

BACKGROUND OF THE INVENTION

The pharmaceutical use of antibodies has increased over the past years. In many instances such antibodies are either injected or infused via the intravenous (IV) route. Unfortunately the amount of antibody that can be administered via the intravenous route is limited by the physico-chemical properties of the antibody, in particularly by its solubility and stability in a suitable liquid formulation and by the volume of the infusion fluid. Alternative administration pathways are subcutaneous or intramuscular injection. These injection pathways require high protein concentration in the final solution to be injected (Shire et al., "Challenges in the development of high protein concentration formulations", J. Pharm. Sci. 2004; 93(6): 1390-1402; Roskos et al., "The clinical pharmacology of therapeutic antibodies", Drug Development Research 2004; 61(3): 108-120. In order to increase the volume, and thereby the therapeutic dose, which can be safely and comfortably administered subcutaneously it has been proposed to use glycosaminoglycanase enzyme(s) in order to increase the interstitial space into which the antibody formulation can be injected (WO2006/091871).

Examples of stable formulations of pharmaceutically active antibodies for therapeutic use currently on the market are as follows:

RITUXAN®/MABTHERA® (Rituximab) is a chimeric antibody which binds to the CD20 antigen on B-cells. The commercial formulation is a sterile, clear, colorless, preservative-free liquid concentrate for intravenous (IV) administration. Rituximab is supplied at a concentration of 10 mg/mL (10 mL) in either 100 mg or 500 mg (50 mL) single-use vials. The product is formulated in 9 mg/mL sodium chloride, 7.35 mg/mL sodium citrate dehydrate, 0.7 mg/mL polysorbate 80, and Water for Injection. The pH is adjusted to 6.5. An alternative liquid formulation for Rituximab suitable for IV administration is disclosed in U.S. Pat. No. 6,991,790.

HERCEPTIN® (Trastuzumab) is a monoclonal antibody directed against the HER2 receptor (anti-HER2) which is currently marketed in Europe in form of a 150 mg lyophilized powder (containing the antibody, α,α-trehalose dihydrate, L-histidine and L-histidine hydrochloride and polysorbate 20) which should be reconstituted with water for injection to yield injection dose of approximately 21 mg/ml. In the USA and many other countries a multiple dosage vial containing 440 mg Trastuzumab is marketed.

AVASTIN® (Bevacizumab) is a monoclonal antibody directed against the vascular endothelial growth factor (VEGF) which is currently marketed in Europe as a liquid formulation in two types of vials: a) 100 mg Bevacizumab in 4 ml and b) 400 mg Bevacizumab in 16 ml, respectively, providing a final concentration of 25 mg/ml in water for injection containing the following excipients: trehalose dihydrate, sodium phosphate and polysorbate 20.

While the above antibody formulations have been found suitable for use for intravenous administration there is a desire to provide highly concentrated, stable pharmaceutical formulations of therapeutically active antibodies for subcutaneous injection. The advantage of subcutaneous injections is that it allows the medical practitioner to perform it in a rather short intervention with the patient. Moreover the patient can be trained to perform the subcutaneous injection by himself. Usually injections via the subcutaneous route are limited to approximately 2 ml. For patients requiring multiple doses, several unit dose formulations can be injected at multiple sites of the body surface.

The following two antibody products for subcutaneous administration are already on the market.

HUMIRA® (Adalimumab) is a monoclonal antibody directed against tumor necrosis factor alpha (TNF alpha) which is currently marketed in Europe in form of a 40 mg dose in 0.8 ml injection volume for subcutaneous application (concentration: 50 mg antibody/ml injection volume).

XOLAIR® (Omalizumab) a monoclonal antibody directed against immunoglobulin E (anti-IgE) which is currently marketed in form of a 150 mg lyophilized powder (containing the antibody, sucrose, histidine and histidine hydrochloride monohydrate and polysorbate 20) which should be reconstituted with water for subcutaneous injection to yield a 125 mg/ml injection dose.

No highly concentrated, stable pharmaceutical anti-CD20 antibody formulation suitable for subcutaneous administration is currently available on the market. There is therefore a desire to provide such highly concentrated, stable pharmaceutical formulations of therapeutically active antibodies for subcutaneous injection.

The injection of parenteral drugs into the hypodermis is generally limited to volumes of less than 2 ml due to this viscoelastic resistance to hydraulic conductance in the subcutaneous (SC) tissue and generated backpressure upon injection (Aukland K. and Reed R., "Interstitial-Lymphatic Mechanisms in the control of Extracellular Fluid Volume", Physiology Reviews", 73:1-78 (1993)) as well as due to the perceptions of pain.

The preparation of high concentration protein formulations is very challenging and there is a need to adapt each formulation to the particular proteins used because each protein has a different aggregation behavior. Aggregates are suspected to cause immunogenicity of therapeutic proteins in at least some of the cases. Immunogenic reaction against protein or antibody aggregates may lead to neutralizing antibodies which may render the therapeutic protein or antibody ineffective. It appears that the immunogenicity of protein aggregates is most problematic in connection with subcutaneous injections, whereby repeated administration increases the risk of an immune response.

While antibodies have a very similar overall structure, such antibodies differ in the amino acid composition (in particular in the CDR regions responsible for the binding to the antigen) and the glycosylation pattern. Moreover there may additionally be post-translational modifications such as charge and glycosylation variants.

SUMMARY OF THE INVENTION

The present invention provides a highly concentrated, stable pharmaceutical formulation of a pharmaceutically active anti-CD20 antibody or a mixture of such antibody molecules, preferably for subcutaneous injection.

More particularly the highly concentrated, stable pharmaceutical formulation of a pharmaceutically active anti-CD20 antibody formulation of the present invention comprises:
  about 20 to 350 mg/ml anti-CD20 antibody;
  about 1 to 100 mM of a buffering agent providing a pH of 5.5±2.0;
  about 1 to 500 mM of a stabilizer or a mixture of two or more stabilizers, whereby optionally methionine is used as a secondary stabilizer, preferably in a concentration of 5 to 25 mM;
  0.01 to 0.1% of a nonionic surfactant; and
  Preferably an effective amount of at least one hyaluronidase enzyme.

DETAILED DESCRIPTION OF THE INVENTION

The term "antibody" herein is used in the broadest sense and specifically covers full length antibodies, genetically engineered antibodies like monoclonal antibodies, or recombinant antibodies, polyclonal antibodies, multispecific antibodies (e.g. bispecific antibodies) formed from at least two full length antibodies, chimeric antibodies, humanized antibodies, fully human antibodies, and as well as fragments of such antibodies as long as they exhibit the desired biological activity.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al, Nature, 256:495 (1975), or may be made by recombinant DNA methods (see, e.g., U.S. Pat. No. 4,816,567). The "monoclonal antibodies" may also be isolated from phage antibody libraries using the techniques described in Clarkson et al., Nature, 352:624-628 (1991) and Marks et al., J. Mol. Biol., 222:581-597 (1991). The terms "monoclonal antibody" or "monoclonal antibody composition" as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell. The term "monoclonal antibodies" herein specifically include the so-called chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of a full length antibody, generally at least the antigen binding portion or the variable region thereof. Examples of antibody fragments include Fab, Fab', F(ab')$_2$, and Fv fragments; diabodies, single-chain antibody molecules, immunotoxins, and multispecific antibodies formed from antibody fragments. In addition, antibody fragments comprise single chain polypeptides having the characteristics of a VH chain, namely being able to assemble together with a VL chain binding to the CD20 antigen. "Antibody fragments" also comprise such fragments which per se are not able to provide effector functions (ADCC/CDC) but provide this function in a manner according to the invention after being combined with appropriate antibody constant domain(s).

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. Preferably, the full length antibody has one or more effector functions.

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include acidic variant (e.g. deamidated antibody variant), basic variant, the antibody with an amino-terminal leader extension (e.g. VHS-) on one or two light chains thereof, antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations. Moreover the term "glycosylation variant" includes also glycoengineered antibodies such as those described in WO 1,331,266 and U.S. Pat. No. 7,517,670.

Antibody "effector functions" refer to those biological activities attributable to the Fc region (a native sequence Fc region or amino acid sequence variant Fc region) of an antibody. Examples of antibody effector functions include Clq binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α (alpha), δ (delta), ε (epsilon), γ (gamma), and μ (mu), respectively. The subunit structures and three-dimensional configurations of different classes of immunoglobulins are well known.

Herein, "biological activity" of a monoclonal antibody refers to the ability of the antibody to bind to antigen and result in a measurable biological response which can be measured in vitro or in vivo. Such activity may be antagonistic (for example where the antibody is a CD20 antibody) or agonistic.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted below for chimeric and bifunctional antibodies. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. See, e.g., Riechmann, L., et al., Nature 332 (1988) 323-327; and Neuberger, M. S., et al., Nature 314 (1985) 268-270.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. No. 5,202,238 and U.S. Pat. No. 5,204,244.

The term "human antibody", as used herein, is intended to include antibodies having variable and constant regions derived from human germline immunoglobulin sequences. Human antibodies are well-known in the state of the art (van Dijk, M. A., and van de Winkel, J. G., Curr. Opin. Pharmacol. 5 (2001) 368-374). Based on such technology, human antibodies against a great variety of targets can be produced. Examples of human antibodies are for example described in Kellermann, S. A., et al., Curr Opin Biotechnol. 13 (2002) 593-597.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, may not naturally exist within the human antibody germline repertoire in vivo.

As used herein, "specifically binding" or "binds specifically to" refers to an antibody specifically binding to the CD20 antigen. Preferably the binding affinity is of Kd value of $10^{-9}$ mol/l or lower (e.g. $10^{-10}$ mol/l), preferably with a Kd value of $10^{-10}$ mol/l or lower (e.g. $10^{-12}$ mol/l). The binding affinity is determined with a standard binding assay, such as surface plasmon resonance technique (BIA-CORE®).

The term "nucleic acid molecule", as used herein, is intended to include DNA molecules and RNA molecules. A nucleic acid molecule may be single-stranded or double-stranded, but preferably is double-stranded DNA.

The "constant domains" are not involved directly in binding the antibody to an antigen but are involved in the effector functions (ADCC, complement binding, and CDC).

The "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the b-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat, et al., Sequences of Proteins of Immunological Interest, 5th Ed. Public Health Service, National Institutes of Health, Bethesda, Md. (1991)) and/or those residues from a "hypervariable loop".

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: antibody dependent cellular cytotoxicity (ADCC), complement-dependent cytotoxity (CDC), inducing cell death and/or apoptosis, homotypic aggregation etc.

Synonyms of CD20, as recognized in the art, include B-lymphocyte antigen CD20, B-lymphocyte surface antigen B1, Leu-16, and Bp35.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al, Blood 103 (2004) 2738-2743; and Cragg, M. S., et al Blood 101 (2003) 1045-1051, see Table 1:

TABLE 1

Properties of Type I and Type II anti-CD20 Antibodies

| Type I anti-CD20 antibodies | Type II anti-CD20 antibodies |
|---|---|
| Type I CD20 epitope | Type II CD20 epitope |
| Localize CD20 to lipid rafts | Do not localize CD20 to lipid rafts |

TABLE 1-continued

Properties of Type I and Type II anti-CD20 Antibodies

| Type I anti-CD20 antibodies | Type II anti-CD20 antibodies |
|---|---|
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

One essential property of type I and type II anti-CD20 antibody is their mode of binding. Thus type I and type II anti-CD20 antibody can be classified by the ratio of the binding capacities to CD20 on Raji cells (ATCC-No. CCL-86) of said anti-CD20 antibody compared to rituximab.

As used herein, "anti-CD20 antibody" can be either a type I or type II antibody. Preferably, it is a type I antibody, most preferred it is rituximab.

The type I anti-CD20 antibodies have a ratio of the binding capacities to CD20 on Raji cells (ATCC No. CCL-86) of said anti-CD20 antibody compared to rituximab of 0.8 to 1.2, preferably of 0.9 to 1.1. Examples of such type I anti-CD20 antibodies include e.g. Rituximab, in U.S. Pat. No. 7,381,560 (Anderson et. al., see e.g. FIGS. 4 and 5), 1F5 IgG2a (ECACC, hybridoma; Press et al., Blood 69/2:584-591 (1987)), HI47 IgG3 (ECACC, hybridoma), 2C6 IgG1 (as disclosed in WO2005/103081), 2F2 IgG1 or ofatumumab (as disclosed and WO 2004/035607 and WO2005/103081) and 2H7 IgG1 (as disclosed in WO 2004/056312) and WO 2006/084264 (e.g. the variants disclosed in tables 1 and 2). Preferably said type I anti-CD20 antibody is a monoclonal antibody that binds to the same epitope as rituximab.

The type II anti-CD20 antibodies have a ratio of the binding capacities to CD20 on Raji cells (ATCC No. CCL-86) of said anti-CD20 antibody compared to Rituximab of 0.3 to 0.6, preferably of 0.35 to 0.55, more preferably 0.4 to 0.5. Examples of such type II anti-CD20 antibodies include e.g. tositumomab (B1 IgG2a), humanized B-Ly1 antibody IgG1 (a chimeric humanized IgG1 antibody as disclosed in WO2005/044859), 11B8 IgG1 (as disclosed in WO 2004/035607), and AT80 IgG1. Preferably said type II anti-CD20 antibody is a monoclonal antibody that binds to the same epitope as humanized B-Ly1 antibody (as disclosed in WO2005/044859).

The "ratio of the binding capacities to CD20 on Raji cells (ATCC-No. CCL-86) of an anti-CD20 antibodies compared to rituximab" is determined by direct immunofluorescence measurement (the mean fluorescent intensities (MFI) is measured) using said anti-CD20 antibody conjugated with Cy5 and rituximab conjugated with Cy5 in a FACSArray (Becton Dickinson) with Raji cells (ATCC-No. CCL-86), and calculated as follows:

$$\text{Ratio of the binding capacities to } CD20 \text{ on Raji cells}$$

$$(ATTC\text{-No. } CCL\text{-}86) = \frac{MFI(Cy5\text{-anti-}CD20 \text{ antibody})}{MFI(Cy5\text{-rituximab})} \times \frac{Cy5\text{-labeling ratio}(Cy5\text{-rituximab})}{Cy5\text{-labeling ratio}(Cy5\text{-anti-}CD20 \text{ antibody})}$$

MFI is the mean fluorescent intensity. The "Cy5-labeling ratio" as used herein means number of Cy5-label molecules per molecule antibody.

Typically said type I anti-CD20 antibody has a ratio of the binding capacities to CD20 on Raji cells (ATCC-No. CCL-86) of said first anti-CD20 antibody compared to rituximab of 0.8 to 1.2, preferably 0.9 to 1.1.

Typically said type II anti-CD20 antibody has a ratio of the binding capacities to CD20 on Raji cells (ATCC-No. CCL-86) of said second anti-CD20 antibody compared to rituximab of 0.3 to 0.6, preferably 0.35 to 0.55, more preferably 0.4 to 0.5.

In a preferred embodiment said type II anti-CD20 antibody, preferably a humanized B-Lyl antibody, has increased antibody dependent cellular cytotoxicity (ADCC).

By "antibody having increased antibody dependent cellular cytotoxicity (ADCC)" is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;

3) the assay is carried out according to following protocol:

i) the PBMCs are isolated using standard density centrifugation procedures and are suspended at $5\times10^6$ cells/ml in RPMI cell culture medium;

ii) the target cells are grown by standard tissue culture methods, harvested from the exponential growth phase with a viability higher than 90%, washed in RPMI cell culture medium, labeled with 100 micro-Curies of $^{51}$CI washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (VN) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector:target cell ratio of 25:1 and the plates are placed in an incubator under 5% CO2 atmosphere at 37 C for 4 hours;

ix) the cell-free supernatant from each well is harvested and the experimentally released radioactivity (ER) is quantified using a gamma counter;

x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point V above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

Said "increased ADCC" can be obtained by glycoengineering of said antibodies, that means enhance said natural, cell-mediated effector functions of monoclonal antibodies by engineering their oligosaccharide component as described in Umana, P. et al., Nature Biotechnol. 17:176-180 (1999) and U.S. Pat. No. 6,602,684.

The term "complement-dependent cytotoxicity (CDC)" refers to lysis of human tumor target cells by the antibody according to the invention in the presence of complement. CDC is measured preferably by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. The assay is performed preferably with $^{51}$Cr or Eu labeled tumor cells and measurement of released $^{51}$Cr or Eu. Controls include the incubation of the tumor target cells with complement but without the antibody.

Typically type I and type II anti-CD20 antibodies of the IgG1 isotype show characteristic CDC properties. Type I anti-CD20 antibodies have and increased CDC (if IgG1 isotype) and type II anti-CD20 antibodies have a decreased CDC (if IgG1 isotype) compared to each other. Preferably both type I and type II anti-CD20 antibodies are IgG1 isotype antibodies.

The "rituximab" antibody is a genetically engineered chimeric human gamma 1 murine constant domain containing monoclonal antibody directed against the human CD20 antigen. This chimeric antibody contains human gamma 1 constant domains and is identified by the name "C2B8" in EP2000149B1 and U.S. Pat. No. 7,381,560 (Anderson et. al., see e.g. FIGS. 4 and 5). Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff et. al, Blood 83(2): 435-445 (1994)). Additionally, it exhibits significant activity in assays that measure antibody-dependent cellular cytotoxicity (ADCC).

The term "humanized B-Lyl antibody" refers to humanized B-Lyl antibody as disclosed in WO2005/044859, which were obtained from the murine monoclonal anti-CD20 antibody B-Lyl (variable region of the murine heavy chain (VH); variable region of the murine light chain (VL); see Poppema, S. and Visser, L., Biotest Bulletin 3: 131-139 (1987)) by chimerization with a human constant domain from IgG1 and following humanization (see WO2005/044859). These "humanized B-Lyl antibodies" are disclosed in detail in WO2005/044859.

Preferably the "humanized B-Lyl antibody" has variable region of the heavy chain (VH) selected from group of B-HH2 to BHH9 and B-HL8 to B-HL17 of WO2005/

044859. Especially preferred are B-HH2, BHH-3, B-HH6, BHH8, B-HL8, B-HL11 and B-HL13 of WO2005/044859. Most preferably, said VH is BHH6. Preferably the "humanized B-Lyl antibody" has variable region of the light chain (VL) of B-KV1 of WO2005/044859. Furthermore the humanized B-Lyl antibody is preferably an IgGl antibody. Preferably such humanized B-Lyl antibodies are glycoengineered (GE) in the Fc region according to the procedures described in WO2005/044859, WO 2004/065540, Umana, P. et al., Nature Biotechnol. 17:176-180 (1999) and WO 99/154342. Most glycoengineered humanized B-Lyl antibodies have an altered pattern of glycosylation in the Fc region, preferably having a reduced level of fucose residues. Preferably at least 40% or more (in one embodiment between 40% and 60%, in another embodiment at least 50%, and in still another embodiment at least 70% or more) of the oligosaccharides of the Fc region are non-fucosylated. Furthermore the oligosaccharides of the Fc region are preferably bisected. Most preferably, the "humanized B-Lyl antibody" comprises VH B-HH6 and VL B-KV1 of WO2005/044859. As used herein, said antibody is also referred to as "HuMab<CD20>". Said antibody was designated with the INN Afutuzumab. In another most preferable embodiment, said antibody has a reduced level of fucose residues as defined above and/or the oligosaccharides of the Fc region are most preferably bisected. In yet another most preferable embodiment, said antibody displays increased ADCC as defined herein.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., Nature Biotechnol. 14:975-81 (1996)).

Mammalian cells are the preferred hosts for production of therapeutic glycoproteins, due to their capability to glycosylate proteins in the most compatible form for human application. (Cumming et al., Glycobiology 1:115-30 (1991); Jenkins et al., Nature Biotechnol. 14:975-81 (1996)). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serumfree media, and permit the development of safe and reproducible bioprocesses. Other commonly used animal cells include baby hamster kidney (BHK) cells, NS0- and SP2/0-mouse myeloma cells. More recently, production from transgenic animals has also been tested. (Jenkins et al., Nature Biotechnol. 14: 975-981 (1996)).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Monison, S. L., Trends Biotech. 15: 26-32 (1997)). The structure of the attached N-linked carbohydrate varies considerably, depending on the degree of processing, and can include highmannose, multiply-branched as well as biantennary complex oligosaccharides. (Wright, A., and Morrison, S. L., Trends Biotech. 15: 26-32 (1997)). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R. et al., Glycobiology 5(8):813-22 (1995)).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P. et al., Nature Biotechnol. 17:176-180 (1999) and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5: 813-822 (1995); Jefferis, R., et al., Immunol. Rev. 163: 59-76 (1998); Wright, A. and Morrison, S. L., Trends Biotechnol. 15: 26-32 (1997)).

It was previously shown that overexpression in Chinese hamster ovary (CHO) cells of β(1,4)-N-acetylglucosaminyl-transferase III ("GnTIII") a glycosyltransferase catalyzing the formation of bisected oligosaccharides, significantly increases the in vitro ADCC activity of an antineuroblastoma chimeric monoclonal antibody (chCE7) produced by the engineered CHO cells. (See Umana, P. et al., Nature Biotechnol. 17: 176-180 (1999); and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umaña, P., et al., Nature Biotechnol. 17: 176-180 (1999)). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

The term "expression of the CD20" antigen is intended to indicate an significant level of expression of the CD20 antigen in a cell, preferably on the cell surface of a B-Cell, more preferably a B-cell, from a tumor or cancer, respectively, preferably a non-solid tumor. Patients having a "CD20 expressing cancer" can be determined by standard assays known in the art. "Expression of the CD20" antigen is also preferable intended to indicate an significant level of expression of the CD20 antigen in a cell, preferably on the cell surface of a B-Cell, more preferably a B-cell, in an autoimmune disease, e.g. CD20 antigen expression is measured using immunohistochemical (IHC) detection, FACS or via PCR-based detection of the corresponding mRNA.

The term "CD20 expressing cancer" as used herein refers preferably to lymphomas (preferably B-Cell Non-Hodgkin's lymphomas (NHL)) and lymphocytic leukemias. Such lymphomas and lymphocytic leukemias include e.g.: (a) follicular lymphomas, (b) Small Non-Cleaved Cell Lymphomas/Burkitt's lymphoma (including endemic Burkitt's lymphoma, sporadic Burkitt's lymphoma and Non-Burkitt's lymphoma), (c) marginal zone lymphomas (including extranodal marginal zone B cell lymphoma (Mucosa-associated lymphatic tissue lymphomas, MALT), nodal marginal zone B cell lymphoma and splenic marginal zone lymphoma), (d) Mantle cell lymphoma (MCL), (e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), (f) hairy cell leukemia, (g) lymphocytic lymphoma, Waldenstrom's macroglobulinemia, (h) acute lymphocytic leukemia (ALL), chronic lymphocytic leukemia (CLL), small lymphocytic lymphoma (SLL), B-cell prolymphocytic leukemia, (i) plasma cell neoplasms, plasma cell myeloma, multiple myeloma, plasmacytoma, and (j) Hodgkin's disease.

Preferably the CD20 expressing cancer is a B-Cell Non-Hodgkin's lymphomas (NHL). Other examples of CD20 expressing cancers include: Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, Waldenstrom's macroglobulinemia, or primary CNS lymphoma.

As used herein, "autoimmune disease" relates to a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens Johnson syndrome, pemphigoid bullous, pemphigus, autoimmune polyendocrinopathies, s nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular I endocrinopathy syndromes), Type I diabetes also referred to as insulin-dependent diabetes i mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

A "growth inhibitory agent" when used herein refers to a compound or composition which inhibits growth of a cell, especially a CD20 expressing cancer cell either in vitro or in vivo. Thus, the growth inhibitory agent may be one which significantly reduces the percentage of CD20 expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "The Molecular Basis of Cancer", Mendelsohn and Israel, eds., Chapter 1, entitled "Cell cycle regulation, oncogenes, and antineoplastic drugs" by Murakami et al. (WB Saunders: Philadelphia, 1995), especially p. 13.

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelarnine); acetogenins (especially bullatacin and bullatacinone); delta-9-tetrahydrocannabinol (dronabinol, MARENOL™); beta-lapachone; lapachol; colchicines; betulinic acid; a camptothecin (including the synthetic analogue topotecan (HYCAMTIN™), CPT-11 (irinotecan, CAMPTOSAR™), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptoplhycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranirnnustine; antibiotics such as the enediyne antibiotics (e. g., calicheamicin, especially calicheamicin gamma 11 and calicheamicin omega 11 (see, e.g., Angew, Chemie Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN™, morpholino-doxorubicin, cyanomorpholino-doxorubicin, 2-pyrrolino-doxorubicin, doxorubicin HCl liposome injection (DOXIL™), liposomal doxorubicin TLC D-99 (MYOCET™), peglylated liposomal doxorubicin (CAELYX™), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR™), tegafur (UFTORAL™), capecitabine (XELODA™), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSKL™ polysaccharide complex (JHS Natural Products, Eugene, Oreg.); razoxane; rhizoxin; sizofiran; spirogermaraium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL™), albumin-engineered nanoparticle formulation of paclitaxel (ABRAXANE™), and docetaxel (TAXOTERE™); chloranbucil; 6-thioguanine; mercaptopurine; metliotrexate; platinum agents such as cisplatin, oxaliplatin, and carboplatin; vincas, which prevent tubulin polymerization from forming microtubules, including vinblastine (VELBAN™), vincristine (ONCOVIN™), vindesine (ELDISINE™, FILDESIN™), and vinorelbine (NAVELBINE™)); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN™); bisphosphonates such as clodronate (for example, BONEFOS™ or OSTAC™), etidronate (DIDROCAL™), NE-58095, zoledronic acid/zoledronate (ZOMETA™), alendronate (FOSAMAJX™), pamidronate (AREDIA™), tiludronate (SKELID™), or risedronate (ACTONEL™); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE™ vaccine and gene therapy vaccines, for example, ALLOVECTIN™ vaccine, LEUVECTIN™ vaccine, and VAXID™ vaccine; topoisomerase 1 inhibitor (e.g., LURTOTECAN™); rmRH (e.g., ABARELIX™); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE™); CCI-779; tipifarnib (R11577); orafenib, ABT510; Bcl-2 inhibitor such as oblimersen sodium (GENASENSE™); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone (optionally further comprising interferon-α (CHVP/interferon-α), FOLFOX, an abbreviation for a treatment regimen with oxaliplatin (ELOXATIN™) combined with 5-FU and leucovovin, CVP (cyclophosphamide, vincristine, and prednisolone), MCP (mitozantrone, chlorambucil and prednisolone), FC (fludarabine and cyclophosphamide), ICE (ifosfamide, carboplatin, and etoposide), and dexamethasone, cytarabine, and cisplatin (DHAP), dexamethasone, doxorubicin liposomal, and vincristine (DVD) etc.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as Bevacizumab (AVASTIN™).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin; prorelaxin, glycoprotein hormones such as follicle stimulating hormone (FSH), thyroid stimulating hormone (TSH), and luteinizing hormone (LH), hepatic growth factor; fibroblast growth factor, prolactin, placental lactogen, tumor necrosis factor α and β, mullerian-inhibiting substance, mouse gonadotropin-associated peptide, inhibin; activin, vascular endothelial growth factor, integrin, thrombopoietin (TPO), nerve growth factors such as NGF-β, platelet-growth factor; transforming growth factors (TGFs) such as TGF-α and TGF-β, insulin-like growth factor-I and -II, erythropoietin (EPO), osteoinductive factors; interferons such as interferon-α, -β, and -γ, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1α, IL-2, IL-3, IL-4, IL-5, IL-6, IL-7, IL-8, IL-9, IL-10, IL-11, IL-12, a tumor necrosis factor such as TNF-α or TNF-β, and other polypeptide factors including LIF and kit ligand (KL). As used herein, the term cytokine includes proteins from natural sources or from recombinant cell culture and biologically active equivalents of the native sequence cytokines The term "effective amount" refers to an amount which provides the desired effect. In the case of a formulation ingredient such as the hyaluronidase enzyme in accordance with the present invention an effective amount is the amount necessary to increase the dispersion and absorption of the co-administered anti-CD20 antibody in such a way that the anti-CD20 antibody can act in a therapeutically effective way as outline above. In the case of a pharmaceutical drug substance it is the amount of active ingredient effective to treat a disease in the patient. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response, PR, or complete response, CR), increase overall survival time, and/or improve one or more symptoms of cancer.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

A "stable" formulation is one in which all the protein therein essentially retain their physical stability and/or chemical stability and/or biological activity upon storage at the intended storage temperature, e.g. 2-8° C. Preferably, the formulation essentially retains its physical and chemical stability, as well as its biological activity upon storage. The storage period is generally selected based on the intended shelf-life of the formulation. Furthermore, the formulation is preferably stable following freezing (to, e.g., −20° C.) and thawing of the formulation, for example following 1 or more cycles of freezing and thawing. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; SDS-PAGE analysis to compare reduced and intact antibody; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), etc.

Therapeutic formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed.

The term "surfactant" as used herein denotes a pharmaceutically acceptable surface-active agent. In the formulation of the invention, the amount of surfactant is described a percentage expressed in weight/volume. The most commonly used weight/volume unit is mg/mL. Suitable examples of pharmaceutically acceptable surfactants include polyoxyethylen-sorbitan fatty acid esters (Tween), polyethylene-polypropylene glycols, polyoxyethylene-stearates, polyoxyethylene alkyl ethers, e.g. polyoxyethylene monolauryl ether, alkylphenylpolyoxy-ethylene ethers (Triton-X), polyoxyethylene-polyoxypropylene copolymer (Poloxamer, Pluronic), and sodium dodecyl sulphate (SDS). Most suitable polyoxyethylenesorbitan-fatty acid esters are polysorbate 20, (sold under the trademark Tween 20™) and polysorbate 80 (sold under the trademark Tween 80™). Most suitable polyethylene-polypropylene copolymers are those sold under the names Pluronic® F68 or Poloxamer 188™. Preferred polyoxyethylene-stearates are those sold under the trademark Myrj™. Most suitable polyoxy-ethylene alkyl ethers are those sold under the trademark Brij™ Most suitable alkylphenolpoly-oxyethylene ethers are sold under the trade name Triton-X.

The term "buffer" as used herein denotes a pharmaceutically acceptable buffer. As used herein the term "buffering agent providing a pH of 5.5±2.0" refers to an agent which provides that the solution comprising it resists changes in pH by the action of its acid/base conjugate components. Suitable pharmaceutically acceptable buffers according to the invention comprise but are not limited to histidine-buffers, citrate-buffers, gluconate-buffers, succinate-buffers, acetate-buffers glycylglycine and other organic acid buffers, and phosphate-buffers. Preferred buffers comprise L-histidine or mixtures of L-histidine with L-histidine hydrochloride with isotonicity agents and potentially pH adjustment with an acid or a base known in the art. Most preferred is L-histidine.

A "histidine buffer" is a buffer comprising the amino acid histidine. Examples of histidine buffers include histidine chloride, histidine acetate, histidine phosphate, histidine sulfate. The preferred histidine buffer identified in the examples herein was found to be histidine chloride. In the preferred embodiment, the histidine chloride buffer is prepared by titrating L-histidine (free base, solid) with diluted hydrochloric acid or by dissolving L-histidine and L-histidine hydrochloride (e.g. as monohydrate) in a defined amount and ratio.

By "isotonic" is meant that the formulation of interest has essentially the same osmotic pressure as human blood. Isotonic formulations will generally have an osmolality of ~300 mOsm/kg. Isotonicity can be measured using a vapor pressure or freezing-point depression type osmometer.

The term "isotonicity agents" as used herein denotes pharmaceutically acceptable isotonicity agents. Isotonicity agents are used to provide an isotonic formulation. An isotonic formulation is liquid or liquid reconstituted from a solid form, e.g. a lyophilized form and denotes a solution having the same tonicity as some other solution with which it is compared, such as physiologic salt solution and the blood serum. Suitable isotonicity agents comprise but are not limited to salts, including but not limited to sodium chloride (NaCl) or potassium chloride, sugars and sugar alcohols including but not limited to glucose, sucrose, trehalose or glycerol and any component from the group of amino acids, sugars, salts and combinations thereof. Isotonicity agents are generally used in a total amount of about 5 mM to about 350 mM.

The term "liquid" as used herein in connection with the formulation according to the invention denotes a formulation which is liquid at a temperature of at least about 2 to about 8° C.

The term "lyophilized" as used herein in connection with the formulation according to the invention denotes a formulation which is dried by freezing the formulation and subsequently subliming the ice from the frozen content by any freeze-drying methods known in the art, for example commercially available freeze-drying devices.

The term "salts" as used herein denotes a salt in an amount of about 1 mM to about 500 mM. Non-limiting examples of salts include salts of any combinations of the cations sodium potassium, calcium or magnesium with anions chloride, phosphate, citrate, succinate, sulphate or mixtures thereof.

The term "amino acid" as used herein denotes an amino acid in an amount of about 1 to about 100 mg/mL comprising but not limited to arginine, glycine, ornithine, glutamine, asparagine, lysine, histidine, glutamic acid, aspargic acid, isoleucine, leucine, alanine, phenylalanine, tyrosine, tryptophane, methionine, serine, proline.

A "saccharide" herein comprises the general composition $(CH_2O)_n$ and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. Also included in the definition according to the invention are glucosamine, N-Methylglucosamine (so-called "Meglumine"), galactosamine and neuraminic acid and combinations of the saccharides according to the invention. The preferred saccharide herein is a non-reducing disaccharide, such as trehalose or sucrose. The most preferred saccharide in accordance with the present invention is trehalose.

The term "stabilizer" refers to pharmaceutically acceptable stabilizers, like for example but not limited to amino acids and sugars as described in the above sections as well as commercially available dextrans of any kind and molecular weight as known in the art.

The term "antioxidant" denotes a pharmaceutically acceptable antioxidant. This may include excipients such as methionine, benzylalcohol or any other excipient used to minimize oxidation.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The problem to be solved by the present invention is therefore to provide novel highly concentrated, stable pharmaceutical formulations of a pharmaceutically active anti-CD20 antibody or a mixture of such antibody molecules for subcutaneous injection. Such formulations comprise, in addition to the high amounts of anti-CD20 antibody or mixture thereof, a buffering agent, a stabilizer or a mixture of two or more stabilizers, a nonionic surfactant and preferably an effective amount of at least one hyaluronidase enzyme. The preparation of highly-concentrated antibody formulations is challenging because of a potential increase in viscosity at higher protein concentration and a potential increase in protein aggregation, a phenomenon that is per se concentration-dependent. High viscosities negatively impact the process ability (e.g. pumping and filtration steps) of the antibody formulations and the administration (e.g. the syringe ability). By the addition of excipients high viscosities could be decreased in some cases. Control and analysis of protein aggregation is an increasing challenge. Aggregation is potentially encountered during various steps of the manufacturing process, which include fermentation, purification, formulation and during storage. Different factors, such as temperature, protein concentration, agitation stress, freezing and thawing, solvent and surfactant effects, and chemical modifications, might influence the aggregation behavior of a therapeutic protein. During development of a highly concentrated antibody formulation the aggregation tendency of the protein has to be monitored and controlled by the addition of various excipients and surfactants (Kiese S. et al., J. Pharm. Sci., 2008; 97(10); 4347-4366).

In a first aspect the present invention provides a highly concentrated, stable pharmaceutical formulation of a pharmaceutically active anti-CD20 antibody or a mixture of such antibody molecules for parenteral application. Preferably the route of application is intravenous administration as a bolus or by continuous infusion over a period of time, by intramuscular, intraperitoneal, intracerobrospinal, subcutaneous, intra-articular, intrasynovial, or intrathecal routes. Intravenous or subcutaneous administration of the antibodies is preferred; subcutaneous injection is preferred most. As set out above, it is by far not trivial to generate a highly concentrated, stable, pharmaceutical formulation of a CD20 antibody which is essentially free of particles. If said formulation is intended for subcutaneous application, then in a preferred embodiment said formulation is combined with a hyaluronidase enzyme.

More particularly the highly concentrated, stable pharmaceutical formulation of a pharmaceutically active anti-CD20 antibody formulation of the present invention comprises:
  about 20 to 350 mg/ml anti-CD20 antibody;
  about 1 to 100 mM of a buffering agent providing a pH of 5.5±2.0;

about 1 to 500 mM of a stabilizer or a mixture of two or more stabilizers, whereby optionally methionine is used as a secondary stabilizer, preferably in a concentration of 5 to 25 mM;

0.01 to 0.1% of a nonionic surfactant; and preferably an effective amount of at least one hyaluronidase enzyme.

The highly concentrated, stable pharmaceutical formulation of a pharmaceutically active anti-CD20 antibody formulation of the present invention may be provided in liquid form or may be provided in lyophilized form. The antibody concentration in the reconstituted formulation can be increased by reconstitution of a lyophilized formulation to provide a protein concentration in the reconstituted formulation which is about 2-40 times greater than the protein concentration in the mixture before the lyophilization step.

The preferred anti-CD20 antibody concentration is 50 to 150 mg/ml, more preferred is 75 to 150 mg/ml, even more preferred is 120±20 mg/ml, most preferred is about 120 mg/ml.

The preferred concentration of the buffering agent is 1 to 50 mM, more preferably 10 to 30 mM; the most preferred concentration is about 20 mM. Various buffering agents are known to the person skilled in the art as outlined above. The preferred buffering agent is selected from the group consisting of a histidine buffer, acetic acid buffer, and citric acid buffer, most preferably a L-histidine/HCl buffer. The histidine-buffer according to the invention is used in an amount of about 1 mM to about 50 mM, preferably of about 10 mM to about 30 mM and still more preferably of about 20 mM. The acetic acid buffer according to the invention is preferably of about 10 mM to about 30 mM and most preferably of about 20 mM. The citric acid buffer according to the invention is preferably of about 10 mM to about 30 mM and most preferably of about 20 mM.

Independently from the buffer used, the pH will be adjusted at a value comprising about 4.5 to about 7.0 and preferably about 5.5 to about 6.5, also preferably selected from the group consisting of 5.5, 6.0, 6.1 and 6.5. This pH can be obtained by adjustment with an acid or base known in the art or by using adequate mixtures of buffer components or both.

The stabilizer(s) (used synonymously with the term "stabilizing agent" in the present patent description) is/are preferably selected from the group consisting of a salt, a carbohydrate, saccharide and amino acid(s), more preferably a carbohydrate or saccharide, more preferably a sugar admitted by the authorities as a suitable additive or excipient in pharmaceutical formulations, most preferably selected from the group consisting of α,α-trehalose dihydrate, NaCl and methionine. The preferred concentration of the stabilizer is 15 to 250 mM, or more preferably 150 to 250 mM. Most preferred is a concentration of about 210 mM. The formulation may contain a secondary stabilizer, whereby this secondary stabilizer is preferably methionine, preferably in a concentration of 5 to 25 mM, more preferably in a concentration of 5 to 15 mM. The most preferred methionine concentration is about 10 mM.

The nonionic surfactant is preferably a polysorbate, more preferably is selected from the group of polysorbate 20, polysorbate 80 and polyethylene-polypropylene copolymer. The concentration of the nonionic surfactant is 0.01 to 0.1% (w/v), or 0.02 to 0.08% (w/v) and preferably 0.02 to 0.06% (w/v), most preferably about 0.06% (w/v).

The term "sugar" as used herein denotes a pharmaceutically acceptable sugar used in an amount of about 25 mM to about 500 mM. Preferred is 100 to 300 mM. More preferred is 180 to 240 mM. Most preferred is 210 mM.

The concentration of the hyaluronidase enzyme depends on the actual hyaluronidase enzyme used in the preparation of the formulation in accordance with the invention. An effective amount of the hyaluronidase enzyme can easily be determined by the person skilled in the art based on the disclosure further below. It should be provided in sufficient amount so that an increase in the dispersion and absorption of the co-administered anti-CD20 antibody is possible. The effective amount of the hyaluronidase enzyme is preferably about 1,000 to 16,000 U/ml, whereby the said amount corresponds to about 0.01 mg to 0.15 mg protein based on an assumed specific activity of 100,000 U/mg. The preferred concentration of the hyaluronidase enzyme is about 1,500 to 12,000 U/ml. Most preferred is a concentration of about 2,000 U/ml or about 12,000 U/ml. The amounts specified herein before correspond to the amount of hyaluronidase enzyme initially added to the formulation. The hyaluronidase enzyme is present either as a combined final formulation or for use for co-administration, e.g. as a co-formulation as further outlined below. The important issue for the claimed formulation is that at the time it is ready for use and/or is injected it has the claimed composition.

The hyaluronidase enzyme may be derived from animals, human samples or manufactured based on the recombinant DNA technology as described further below.

More particularly the highly concentrated, stable pharmaceutical formulations in accordance with the present invention have one of the following preferred compositions:

a) 100 to 150 mg/ml anti-CD20 antibody, whereby this antibody is preferably Rituximab, Ocrelizumab or HuMab<CD20>; 1 to 50 mM of a histidine buffer, preferably L-histidine/HCl at a pH of about 5.5; 15 to 250 mM of a stabilizer which is preferably α,α-trehalose dihydrate and optionally methionine as a second stabilizer at a concentration of 5 to 25 mM; a non-ionic surfactant selected from the group of polysorbate 20 and polysorbate 80, preferably 0.02 to 0.06% (w/v), and optionally 1,000 to 16,000 U/ml of a hyaluronidase enzyme, preferably rHuPH20, most preferably at a concentration of 2,000 U/ml or 12,000 U/ml.

b) 120±20 mg/ml anti-CD20 antibody, whereby this antibody is preferably Rituximab, Ocrelizumab or HuMab<CD20>; 10 to 30 mM, preferably 20 mM of a histidine buffer, preferably L-histidine/HCl at a pH of about 5.5; 150 to 250 mM, preferably 210 mM of a stabilizer which is preferably α,α-trehalose dihydrate and optionally methionine as a second stabilizer at a concentration of 5 to 25 mM, preferably 5 to 15 mM, most preferably 10 mM; a non-ionic surfactant selected from the group of polysorbate 20 and polysorbate 80, preferably 0.02 to 0.06% (w/v), and optionally 1,000 to 16,000 U/ml, preferably 1,500 to 12.000 U/ml, most preferably 2,000 U/ml or 12,000 U/ml of a hyaluronidase enzyme, preferably rHuPH20.

c) 120 mg/ml anti-CD20 antibody, whereby this antibody is preferably Rituximab, Ocrelizumab or HuMab<CD20>; 10 to 30 mM, preferably 20 mM of a histidine buffer, preferably L-histidine/HCl at a pH of about 5.5; 150 to 250 mM, preferably 210 mM of a stabilizer which is preferably α,α-trehalose dihydrate and optionally methionine as a second stabilizer at a concentration of 5 to 25 mM, preferably 5 to 15 mM, most preferably 10 mM; a non-ionic surfactant selected from the group of polysorbate 20 and polysorbate 80, preferably 0.02 to 0.06% (w/v), and optionally 1,000 to 16,000 U/ml, preferably 1,500 to 12,000 U/ml, most preferably 2,000 U/ml or 12,000 U/ml of a hyaluronidase enzyme, preferably rHuPH20.

d) 120 mg/ml anti-CD20 antibody, preferably Rituximab; 20 mM of a histidine buffer, preferably L-histidine/HCl at a pH of about 5.5; 210 mM α,α-trehalose dihydrate and optionally 10 mM methionine as a second stabilizer; a non-ionic surfactant selected from the group of polysorbate 20 and polysorbate 80, preferably 0.02 to 0.06% (w/v), and optionally 2,000 U/ml or 12,000 U/ml of a hyaluronidase enzyme, preferably rHuPH20.

e) A lyophilized formulation comprising 120 mg/ml anti-CD20 antibody, preferably Rituximab; 20 mM of a histidine buffer, preferably L-histidine/HCl at a pH of about 5.5; 210 mM of α,α-trehalose dihydrate and optionally 10 mM methionine as a second stabilizer; a non-ionic surfactant selected from the group of polysorbate 20 and polysorbate 80, preferably 0.02 to 0.06% (w/v), and optionally 2,000 U/ml or 12,000 U/ml of a hyaluronidase enzyme, preferably rHuPH20.

A stable pharmaceutical formulation of a pharmaceutically active anti-CD20 antibody is provided comprising about 30 mg/ml to 350 mg/ml, for example about 30 mg/ml to 100 mg/ml (including about 30 mg/ml, about 50 mg/ml or about 100 mg/ml) Ocrelizumab (e.g. humanized 2H7.v16); about 1 to 100 mM of a buffering agent (e.g. sodium acetate) providing a pH of 5.5±2.0 (e.g. pH 5.3); about 15 to 250 mM of a stabilizer or a mixture of two or more stabilizers (including trehalose, e.g. about 8% trehalose dihydrate); about 0.01 to 0.1% (w/v) of a nonionic surfactant; and optionally an effective amount of at least one hyaluronidase enzyme (e.g. rhHUPH20), preferably in an amount from about 1,500 U/ml to about 12,000 U/ml.

Alternative compositions of preferred formulations are given in the examples.

It has been proposed to facilitate the subcutaneous injection of therapeutic proteins and antibodies by using small amounts of soluble hyaluronidase glycoproteins (sHASEGPs); see WO2006/091871. It has been shown that the addition of such soluble hyaluronidase glycoproteins (either as a combined formulation or by co-administration) facilitates the administration of therapeutic drug into the hypodermis. By rapidly depolymerizing hyaluronan HA in the extracellular space sHASEGP reduces the viscosity of the interstitium, thereby increasing hydraulic conductance and allowing for larger volumes to be administered safely and comfortably into the subcutaneous tissue. The increased hydraulic conductance induced by sHASEGP through reduced interstitial viscosity allows for greater dispersion, potentially increasing the systemic bioavailability of SC administered therapeutic drug.

The highly concentrated, stable pharmaceutical formulations of the present invention comprising a soluble hyaluronidase glycoprotein are therefore particularly suited for subcutaneous injection. It is clearly understood by the person skilled in the art that such a formulation comprising an anti-CD20 antibody and a soluble hyaluronidase glycoprotein can be provided for administration in form of one single combined formulation or alternatively in form of two separate formulations which can be mixed just prior to the subcutaneous injection. Alternatively the anti-CD20 antibody and the soluble hyaluronidase glycoprotein can be administered as separate injections at different sites of the body, preferably at sites which are immediately adjacent to each other. It is also possible to inject the therapeutic agents present in the formulation in accordance with the present invention as consecutive injections, e.g. first the soluble hyaluronidase glycoprotein followed by the injection of the anti-CD20 antibody formulation. These injections can also be performed in the reversed order, viz. by first injecting the anti-CD20 antibody formulation followed by injecting the soluble hyaluronidase glycoprotein. In case the anti-CD20 antibody and the soluble hyaluronidase glycoprotein are administered as separate injections, one or both of the proteins have to be provided with the buffering agent, the stabilizer(s) and the nonionic surfactant in the concentrations as specified in the appended claims but excluding the hyaluronidase enzyme. The hyaluronidase enzyme can then be provided e.g. in a L-histidine/HCl buffer at pH of about 6.5, 100 to 150 mM NaCl and 0.01 to 0.1% (w/v) polysorbate 20 or polysorbate 80. In a preferred embodiment the anti-CD20 antibody is provided with the buffering agent, the stabilizer(s) and the nonionic surfactant in the concentrations as specified in the appended claims.

As noted above the soluble hyaluronidase glycoprotein may be considered to be a further excipient in the anti-CD20 formulation. The soluble hyaluronidase glycoprotein may be added to the anti-CD20 formulation at the time of manufacturing the anti-CD20 formulation or may be added shortly before the injection. Alternatively the soluble hyaluronidase glycoprotein may be provided as a separate injection. In the latter case the soluble hyaluronidase glycoprotein may be provided in a separate vial either in lyophilized form which must be reconstituted with suitable diluents before the subcutaneous injection takes place, or my be provided as a liquid formulation by the manufacturer. The anti-CD20 formulation and the soluble hyaluronidase glycoprotein may be procured as separate entities or may also be provided as kits comprising both injection components and suitable instructions for their subcutaneous administration. Suitable instructions for the reconstitution and/or administration of one or both of the formulations may also be provided.

Therefore the present invention also provides pharmaceutical compositions consisting of an a highly concentrated, stable pharmaceutical formulation of a pharmaceutically active anti-CD20 antibody or a mixture of such antibody and a suitable amount of at least one hyaluronidase enzyme in the form of a kit comprising both injection components and suitable instructions for their subcutaneous administration.

A further aspect of the present invention relates to injection devices comprising a highly concentrated, stable pharmaceutical formulation in accordance with the present invention. Such formulation may consist of a pharmaceutically active anti-CD20 antibody or a mixture of such antibody molecules and suitable excipients as outlined below and may additionally comprise a soluble hyaluronidase glycoprotein either as a combined formulation or as a separate formulation for co-administration.

A variety of anti-CD20 antibodies are known in the prior art. Such antibodies are preferably monoclonal antibodies. The may either be so-called chimaeric antibodies, humanized antibodies or fully human antibodies. They may either be full length anti-CD20 antibodies; anti-CD20 antibody fragments having the same biological activity; including amino acid sequence variants and/or glycosylation variants of such antibodies or fragments. Examples of humanized anti-CD20 antibodies are known under the INN names Rituximab, Ocrelizumab and Afutuzumab (HuMab<CD20>). The most successful therapeutic anti-CD20 antibody is Rituximab sold by Genentech Inc. and F. Hoffmann-La Roche Ltd under the trade name MABTHERA® or RITUXAN®.

The anti-CD20 antibody as defined herein is preferably selected from the group of Rituximab (see e.g. U.S. Pat. No. 7,381,560, and EP2000149B1 Anderson et. al., see e.g. FIGS. 4 and 5), Ocrelizumab (as disclosed in WO 2004/

056312) and WO 2006/084264 (e.g. the variants disclosed in tables 1 and 2), preferably the variant v.16 or v.114 or v.511 and Afutuzumab (HuMab<CD20>; see WO2005/044859). The most preferred anti-CD20 antibody is Rituximab. The terms "Rituximab", "Ocrelizumab" and "Afutuzumab" (HuMab<CD20>) encompass all corresponding anti-CD20 antibodies that fullfill the requirements necessary for obtaining a marketing authorization as an identical or biosimilar product in a country or territory selected from the group of countries consisting of the USA, Europe and Japan. Rituximab has the CDR regions defined in U.S. Pat. No. 7,381,560 and EP2000149B1.

A number of a soluble hyaluronidase glycoproteins are known in the prior art. In order to further define the function, the mechanism of action and the properties of such soluble hyaluronidase glycoproteins the following background information is provided.

The SC (hypodermal) interstitial matrix is comprised of a network of fibrous proteins embedded within a viscoelastic gel of glycosaminoglycans. Hyaluronan (HA), a non-sulfated repeating linear disaccharide, is the prominent glycosaminoglycan of the SC tissue. HA is secreted into the interstitium by fibroblasts as a high molecular weight, megadalton viscous polymer that is subsequently degraded locally, in the lymph, and in the liver, through the action of lysosomal hyaluronidases and exoglycosidases. Approximately 50% of the hyaluronan in the body is produced by the SC tissue, where it is found at approximately 0.8 mg/gm wet weight tissue (Aukland K. and Reed R., "Interstitial-Lymphatic Mechanisms in the control of Extracellular Fluid Volume", Physiology Reviews", 73:1-78 (1993)). It is estimated that the average 70 kg adult contains 15 grams of HA, of which 30 percent is turned over (synthesized and degraded) daily (Laurent L. B., et al., "Catabolism of hyaluronan in rabbit skin takes place locally, in lymph nodes and liver", Exp. Physiol. 1991; 76: 695-703). As a major constituent of the gel-like component of the hypodermal matrix, HA contributes significantly to its viscosity.

Glycosaminoglycans (GAGs) are complex linear polysaccharides of the extracellular matrix (ECM). GAGs are characterized by repeating disaccharide structures of an N-substituted hexosamine and an uronic acid (in the case of hyaluronan (HA), chondroitin sulfate (CS), chondroitin (C), dermatan sulfate (DS), heparan sulfate (HS), and heparin (H)), or a galactose (in the case of keratan sulfate (KS)). Except for HA, all exist covalently bound to core proteins. The GAGs with their core proteins are structurally referred to as proteoglycans (PGs).

Hyaluronan (HA) is found in mammals predominantly in connective tissues, skin, cartilage, and in synovial fluid. Hyaluronan is also the main constituent of the vitreous of the eye. In connective tissue, the water of hydration associated with hyaluronan creates hydrated matrices between tissues. Hyaluronan plays a key role in biological phenomena associated with cell motility including rapid development, regeneration, repair, embryogenesis, embryological development, wound healing, angiogenesis, and tumorigenesis (Toole, Cell Biol. Extracell. Matrix, Hay (ed), Plenum Press, New York, 1991; pp. 1384-1386; Bertrand et al., Int. J. Cancer 1992; 52:1-6; Knudson et al., FASEB J. 1993; 7:1233-1241). In addition, hyaluronan levels correlate with tumor aggressiveness (Ozello et al., Cancer Res. 1960; 20:600-604; Takeuchi et al., Cancer Res. 1976; 36:2133-2139; Kimata et al., Cancer Res. 1983; 43:1347-1354).

HA is found in the extracellular matrix of many cells, especially in soft connective tissues. HA has been assigned various physiological functions, such as in water and plasma protein homeostasis (Laurent T. C. et al., FASEB J., 1992; 6: 2397-2404). HA production increases in proliferating cells and may play a role in mitosis. It has also been implicated in locomotion and cell migration. HA seems to play important roles in cell regulation, development, and differentiation (Laurent et al., supra).

HA has widely been used in clinical medicine. Its tissue protective and rheological properties have proved useful in ophthalmic surgery (e.g. to protect the corneal endothelium during cataract surgery). Serum HA is diagnostic of liver disease and various inflammatory conditions, such as rheumatoid arthritis. Interstitial edema caused by accumulation of HA may cause dysfunction in various organs (Laurent et al., supra).

Hyaluronan protein interactions also are involved in the structure of the extracellular matrix or "ground substance".

Hyaluronidases are a group of generally neutral- or acid-active enzymes found throughout the animal kingdom. Hyaluronidases vary with respect to substrate specificity, and mechanism of action (WO 2004/078140). There are three general classes of hyaluronidases:

1. Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates (CS), generally C4-S and C6-S.
2. Bacterial hyaluronidases (EC 4.2.99.1) degrade hyaluronan and, and to various extents, CS and DS. They are endo-beta-N-acetylhexosaminidases that operate by a beta elimination reaction that yields primarily disaccharide end products.
3. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: neutral-active and acid-active enzymes. There are six hyaluronidase-like genes in the human genome, HYAL1, HYAL2, HYAL3, HYAL4, HYALP1 and PH20/SPAM1. HYALP1 is a pseudogene, and HYAL3 has not been shown to possess enzyme activity toward any known substrates. HYAL4 is a chondroitinase and exhibits little activity towards hyaluronan. HYAL1 is the prototypical acid-active enzyme and PH20 is the prototypical neutral-active enzyme. Acid-active hyaluronidases, such as HYAL1 and HYAL2 generally lack catalytic activity at neutral pH (i.e. pH 7). For example, HYAL1 has little catalytic activity in vitro over pH 4.5 (Frost I. G. and Stern, R., "A microtiter-based assay for hyaluronidase activity not requiring specialized reagents", Anal. Biochemistry, 1997; 251:263-269). HYAL2 is an acid-active enzyme with a very low specific activity in vitro.

The hyaluronidase-like enzymes can also be characterized by those which are generally locked to the plasma membrane via a glycosylphosphatidyl inositol anchor such as human HYAL2 and human PH20 (Danilkovitch-Miagkova et al., Proc. Natl. Acad. Sci. USA, 2003; 100(8):4580-4585; Phelps et al., Science 1988; 240(4860): 1780-1782), and those which are generally soluble such as human HYAL1 (Frost, I. G. et al., "Purification, cloning, and expression of human plasma hyaluronidase", Biochem. Biophys. Res. Commun. 1997; 236(1):10-15). However, there are variations from species to species: bovine PH20 for example is very loosely attached to the plasma membrane and is not anchored via a phospholipase sensitive anchor (Lalancette et al, Biol Reprod., 2001; 65(2):628-36). This unique feature of bovine hyaluronidase has permitted the use of the soluble bovine testes hyaluronidase enzyme as an extract for clinical use (Wydase™, Hyalase™) Other PH20 species are lipid anchored enzymes that are generally not soluble without the use of detergents or lipases. For example, human PH20 is anchored to the plasma membrane via a GPI anchor. Attempts to make human PH20 DNA constructs that would not introduce a lipid anchor into the polypeptide resulted in either a catalytically inactive enzyme, or an insoluble enzyme (Arming et al., Eur. J. Biochem., 1997; 1; 247(3): 810-4). Naturally occurring macaque sperm hyaluronidase is found in both a soluble and membrane bound form. While the 64 kDa membrane bound form possesses enzyme activity at pH 7.0, the 54 kDa form is only active at pH 4.0 (Cherr et al., Dev. Biol., 1996; 10; 175(1): 142-53). Thus, soluble forms of PH20 are often lacking enzyme activity under neutral conditions.

As noted above and in accordance with the teachings in WO2006/091871 and U.S. Pat. No. 7,767,429, small amounts of soluble hyaluronidase glycoproteins (sHASEGPs) can be introduced into a formulation in order to facilitate the administration of therapeutic drug into the hypodermis. By rapidly depolymerizing HA in the extracellular space sHASEGP reduces the viscosity of the interstitium, thereby increasing hydraulic conductance and allowing for larger volumes to be administered safely and comfortably into the SC tissue. The increased hydraulic conductance induced by sHASEGP through reduced interstitial viscosity allows for greater dispersion, potentially increasing the systemic bioavailability of SC administered therapeutic drug.

When injected in the hypodermis, the depolymerization of HA by sHASEGP is localized to the injection site in the SC tissue. Experimental evidence shows that the sHASEGP is inactivated locally in the interstitial space with a half life of 13 to 20 minutes in mice, without detectable systemic absorption in blood following single intravenous dose in CD-1 mice. Within the vascular compartment sHASEGP demonstrates a half life of 2.3 and 5 minutes in mice and Cynomolgus monkeys, respectively, with doses up to 0.5 mg/kg. The rapid clearance of sHASEGP, combined with the continual synthesis of the HA substrate in the SC tissue, results in a transient and locally-active permeation enhancement for other co-injected molecules, the effects of which are fully reversible within 24 to 48 hours post administration (Bywaters G. L., et al., "Reconstitution of the dermal barrier to dye spread after Hyaluronidase injection", Br. Med. J., 1951; 2 (4741): 1178-1183).

In addition to its effects on local fluid dispersion, sHASEGP also acts as absorption enhancer. Macromolecules greater than 16 kilodaltons (kDa) are largely excluded from absorption through the capillaries via diffusion and are mostly absorbed via the draining lymph nodes. A subcutaneously administered macromolecule such as e.g. a therapeutic antibody (molecular weight approximately 150 kDa) must therefore traverse the interstitial matrix before reaching the draining lymphatics for subsequent absorption into the vascular compartment. By increasing local dispersion, sHASEGP increases the rate (Ka) of absorption of many macromolecules. This leads to increased peak blood levels ($C_{max}$) and potentially to increased bioavailability relative to SC administration in the absence of sHASEGP (Bookbinder L. H., et al., "A recombinant human enzyme for enhanced interstitial transport of therapeutics", J. Control. Release 2006; 114: 230-241).

Hyaluronidase products of animal origin have been used clinically for over 60 years, primarily to increase the dispersion and absorption of other co-administered drugs and for hypodermoclysis (SC injection/infusion of fluid in large volume) (Frost G. I., "Recombinant human hyaluronidase (rHuPH20): an enabling platform for subcutaneous drug and fluid administration", Expert Opinion on Drug Delivery, 2007; 4: 427-440). The details on the mechanism of action of hyaluronidases have been described in detail in the following publications: Duran-Reynolds F., "A spreading factor in certain snake venoms and its relation to their mode of action", CR Soc Biol Paris, 1938; 69-81; Chain E., "A mucolytic enzyme in testes extracts", Nature 1939; 977-978; Weissmann B., "The transglycosylative action of testicular hyaluronidase", J. Biol. Chem., 1955; 216: 783-94; Tammi, R., Saamanen, A. M., Maibach, H. I., Tammi M., "Degradation of newly synthesized high molecular mass hyaluronan in the epidermal and dermal compartments of human skin in organ culture", J. Invest. Dermatol. 1991; 97:126-130; Laurent, U. B. G., Dahl, L. B., Reed, R. K., "Catabolism of hyaluronan in rabbit skin takes place locally, in lymph nodes and liver", Exp. Physiol. 1991; 76: 695-703; Laurent, T. C. and Fraser, J. R. E., "Degradation of Bioactive Substances: Physiology and Pathophysiology", Henriksen, J. H. (Ed) CRC Press, Boca Raton, Fla.; 1991. pp. 249-265; Harris, E. N., et al., "Endocytic function, glycosaminoglycan specificity, and antibody sensitivity of the recombinant human 190-kDa hyaluronan receptor for endocytosis (HARE)", J. Biol. Chem. 2004; 279:36201-36209; Frost, G. I., "Recombinant human hyaluronidase (rHuPH20): an enabling platform for subcutaneous drug and fluid administration", Expert Opinion on Drug Delivery, 2007; 4: 427-440. Hyaluronidase products approved in EU countries include Hylase® "Dessau" and Hyalase®. Hyaluronidase products of animal origin approved in the US include Vitrase™, Hydase™, and Amphadase™

The safety and efficacy of hyaluronidase products have been widely established. The most significant safety risk identified is hypersensitivity and/or allergenicity, which is thought to be related to the lack of purity of the animal-derived preparations (Frost, G. I., "Recombinant human hyaluronidase (rHuPH20): an enabling platform for subcutaneous drug and fluid administration", Expert Opinion on Drug Delivery, 2007; 4: 427-440). It should be noted that there are differences with respect to the approved dosages of animal-derived hyaluronidases between the UK, Germany and the US. In the UK, the usual dose as an adjuvant to subcutaneous or intramuscular injection is 1500 units, added directly to the injection. In the US, the usual dose used for this purpose is 150 units. In hypodermoclysis, hyaluronidase is used to aid the subcutaneous administration of relatively large volumes of fluids. In the UK, 1500 units of hyaluronidase are generally given with each 500 to 1000 ml of fluid for subcutaneous use. In the US, 150 units are considered adequate for each liter of hypodermoclysis solution. In Germany, 150 to 300 units are considered adequate for this purpose. In the UK, the diffusion of local anesthetics is accelerated by the addition of 1500 units. In Germany and the US 150 units are considered adequate for this purpose. The dosage differences notwithstanding (the dosage in the UK is ten times higher than in the US), no apparent differences in the safety profiles of animal-derived hyaluronidase products marketed in the US and UK, respectively, have been reported.

On Dec. 2, 2005, Halozyme Therapeutics Inc. received approval from the FDA for an injectable formulation of the recombinant human hyaluronidase, rHuPH20 (HYLENEX™). The FDA approved HYLENEX™ at a dose of 150 units for SC administration of the following indications:

as an adjuvant to increase the absorption and dispersion of other injected drugs for hypodermoclysis as an adjunct in SC urography for improving resorption of radiopaque agents.

As part of that regulatory review it was established that rHuPH20 possesses the same properties of enhancing the dispersion and absorption of other injected drugs as the previously approved animal-derived hyaluronidase preparations, but with an improved safety profile. In particular, the use of recombinant human hyaluronidase (rHuPH20) compared with animal-derived hyaluronidases minimizes the potential risk of contamination with animal pathogens and transmissible spongiform encephalopathies.

Soluble Hyaloronidase glycoproteins (sHASEGP), a process for preparing the same and their use in pharmaceutical compositions have been described in WO 2004/078140.

The detailed experimental work as outlined further below has shown that the claimed formulation surprisingly has favorable storage stability and fulfils all necessary requirements for approval by the health authorities.

The hyaluronidase enzyme in the formulation in accordance with the present invention is believed to enhance the delivery of the anti-CD20 antibody to the systemic circulation, e.g. by increasing the absorption of the active substance (it acts as a permeation enhancer). The hyaluronidase enzyme is also believed to increases the delivery of the therapeutic anti-CD20 antibody into the systemic circulation via the subcutaneous application route by the reversible hydrolyzation of hyaluronan, an extracellular component of the SC interstitial tissue. The hydrolysis of hyaluronan in the hypodermis temporarily opens channels in the interstitial space of the SC tissue and thereby improves the delivery of the therapeutic anti-CD20 antibody into the systemic circulation. In addition, the administration shows reduced pain in humans and less volume-derived swelling of the SC tissue.

Hyaluronidase, when administered locally has its entire effect locally. In other word hyaluronidase is inactivated and metabolized locally in minutes and has not been noted to have systemic or long term effects. The rapid inactivation of hyaluronidase within minutes when it enters the blood stream precludes a realistic ability to perform comparable biodistribution studies between different hyaluronidase products. This property also minimizes any potential systemic safety concerns because the hyaluronidase product cannot act at distant sites.

The unifying feature of all hyaluronidase enzymes in accordance with the present invention is their ability to depolymerize hyaluronan, regardless of differences in chemical structure, in species source, in tissue sources, or in the batches of drug product sourced from the same species and tissue. They are unusual in the fact that their activity is the same (except for potency) in spite of having different structures.

The hyaluronidase enzyme in accordance with the formulation of the present invention is characterized by having no adverse effect on the molecular integrity of the anti-CD20 antibody in the stable pharmaceutical formulation described herein. Furthermore, the hyaluronidase enzyme merely modifies the delivery of the anti-CD20 antibody to the systemic circulation but does not possess any properties that could provide or contribute to the therapeutic effects of systemically absorbed anti-CD20 antibody. The hyaluronidase enzyme is not systemically bioavailable and does not adversely affect the molecular integrity of the anti-CD20 antibody at the recommended storage conditions of the stable pharmaceutical formulation in accordance with the invention. It is therefore to be considered as an excipient in the anti-CD20 antibody formulation in accordance with this invention. As it exerts no therapeutic effect it represents a constituent of the pharmaceutical form apart from the therapeutically active anti-CD20 antibody.

A number of suitable hyaluronidase enzymes in accordance with the present invention are known from the prior art. The preferred enzyme is a human hyaluronidase enzyme, most preferably the enzyme known as rHuPH20. rHuPH20 is a member of the family of neutral and acid-active β-1,4 glycosyl hydrolases that depolymerize hyaluronan by the hydrolysis of the β-1,4 linkage between the $C_1$ position of N-acetyl glucosamine and the $C_4$ position of glucuronic acid. Hyaluronan is a polysaccharide found in the intracellular ground substance of connective tissue, such as the subcutaneous interstitial tissue, and of certain specialized tissues, such as the umbilical cord and vitreous humor. The hydrolysis of hyaluronan temporarily decreases the viscosity of the interstitial tissue and promotes the dispersion of injected fluids or of localized transudates or exudates, thus facilitating their absorption. The effects of hyaluronidase are local and reversible with complete reconstitution of the tissue hyaluronan occurring within 24 to 48 hours (Frost, G. I., "Recombinant human hyaluronidase (rHuPH20): an enabling platform for subcutaneous drug and fluid administration", Expert Opinion on Drug Delivery, 2007; 4:427-440). The increase in the permeability of connective tissue through the hydrolysis of hyaluronan correlates with the efficacy of hyaluronidase for their capability to increase the dispersion and absorption of co-administered molecules.

The human genome contains several hyaluronidase genes. Only the PH20 gene product possesses effective hyaluronidase activity under physiologic extracellular conditions and acts as a spreading agent, whereas acid-active hyaluronidases do not have this property.

rHuPH20 is the first and only recombinant human hyaluronidase enzyme currently available for therapeutic use. The human genome contains several hyaluronidase genes; only the PH20 gene product possesses effective hyaluronidase activity under physiologic extracellular conditions and acts as a spreading agent. Naturally occurring human PH20 protein has a lipid anchor attached to the carboxy terminal amino acid that anchors it to the plasma membrane. The rHuPH20 enzyme developed by Halozyme is a truncated deletion variant that lacks such amino acids in the carboxy terminus responsible for the lipid attachment. This gives rise to a soluble, neutral pH-active enzyme similar to the protein found in bovine testes preparations. The rHuPH20 protein is synthesized with a 35 amino acid signal peptide that is removed from the N-terminus during the process of secretion. The mature rHuPH20 protein contains an authentic N-terminal amino acid sequence orthologous to that found in some bovine hyaluronidase preparations.

The PH20 hyaluronidases, including the animal derived PH20 and recombinant human rHuPH20, depolymerize hyaluronan by the hydrolysis of the β-1,4 linkage between the $C_1$ position of N-acetyl glucosamine and the $C_4$ position of glucuronic acid. The tetrasaccharide is the smallest digestion product (Weissmann, B., "The transglycosylative action of testicular hyaluronidase", J. Biol. Chem., 1955; 216: 783-94). This N-acetyl glucosamine/glucuronic acid structure is not found in N-linked glycans of recombinant biological products and therefore rHuPH20 will not affect the glycosylation of antibodies it is formulated with, such as e.g. Rituximab. The rHuPH20 enzyme itself possesses six N-linked glycans per molecule with core structures similar to that found in monoclonal antibodies. As anticipated, these N-linked structures do not change over time, confirming the lack of enzymatic activity of rHuPH20 on these N-linked glycan structures. The short half life of rHuPH20 and the constant synthesis of hyaluronan lead to a short and local action of the enzyme on tissues.

The hyaluronidase enzyme which is an excipient in the subcutaneous formulation in accordance with the present invention is preferably prepared by using recombinant DNA technology. In this way it is ensured that the same protein (identical amino acid sequence) is obtained all the time and that allergic reactions caused by contaminating proteins co-purified during extraction from a tissue is avoided. The hyaluronidase enzyme used in the formulation in accordance with the present invention is preferably a human enzyme, most preferably rHuPH20.

The amino acid sequence of rHuPH20 (HYLENEX™) is well known and available under CAS Registry No. 757971-58-7. The approximate molecular weight is 61 kDa. See, also, U.S. Pat. No. 7,767,429.

Multiple structural and functional comparisons have been performed between naturally sourced mammalian hyaluronidase and PH-20 cDNA clones from humans and other mammals. The PH-20 gene is the gene used for the recombinant product rHuPH20; however the recombinant drug product is a 447 amino acid truncated version of the full protein encoded by the PH-20 gene. Structural similarities with respect to amino acid sequences rarely exceed 60% in any comparison. Functional comparisons show that the activity of rHuPH20 is very similar to that of previously approved hyaluronidase products. This information is consistent with the clinical findings during the past 50 years that regardless of the source of the hyaluronidase, the clinical safety and efficacy of units of hyaluronidase are equivalent.

The use of rHuPH20 in the anti-CD20 antibody SC formulation in accordance with the present invention allows the administration of higher volumes of drug product and to potentially enhance the absorption of subcutaneously administered CD20 antibody, preferably Rituximab into the systemic circulation.

The osmolality of the stable pharmaceutical formulation in accordance with the invention is 350±50 mOsm/kg.

The stable pharmaceutical formulation in accordance with the invention is essentially free from visible (human eye inspection) particles. The sub-visible particles (as measured by light obscuration) should preferably fulfill the following criteria:
  maximum number of particles ≥10 μm per vial->6000
  maximum number of particles ≥25 μm per vial->600

In a further aspect the present invention provides a use of a formulation for the preparation of a medicament useful for treating a disease or disorder amenable to treatment with an anti-CD20 antibody such as preferably cancer or a non-malignant disease in a subject comprising administering the formulation described herein to a subject in an amount effective to treat the said disease or disorder. Preferably the anti-CD20 antibody is co-administered concomitantly or sequentially with a chemotherapeutic agent.

In a further aspect the present invention provides a method of treating a disease or disorder which is amenable to treatment with an anti-CD20 antibody (e.g. cancer (preferred) or a non-malignant disease) in a subject comprising administering the formulation described herein to a subject in an amount effective to treat the said disease or disorder. The cancer or a non-malignant disease will generally involve CD20-expressing cells, such that the CD20 antibody in the therapeutic pharmaceutical SC formulation in accordance with the present invention is able to bind to the affected cells. The cancer is preferably a CD20 expressing cancer. The non-malignant disease that can be treated with the composition in accordance with the present invention is preferably an autoimmune disease as defined herein. Preferably the anti-CD20 antibody is co-administered concomitantly or sequentially with a chemotherapeutic agent.

The addition of the hyaluronidase to the formulation allows increasing the injection volume which can be safely and comfortably administered subcutaneously. The preferred injection volume is 1 to 15 ml. It has been observed that the administration of the formulation in accordance with the present invention increases the dispersion, absorption and the bioavailability of the therapeutic antibody. Large molecules (i.e. >16 kDa) that are administered via the SC route are preferentially absorbed into the vascular compartment through the draining lymphatic fluids (Supersaxo, A., et al., "Effect of Molecular Weight on the Lymphatic Absorption of Water-Soluble Compounds Following Subcutaneous Administration", 1990; 2:167-169; Swartz, M. A., "Advanced Drug Delivery Review, The physiology of the lymphatic system", 2001; 50: 3-20). The rate of introduction of these large molecules into the systemic circulation is thus slowed relative to intravenous infusion, therefore potentially resulting in reduced frequency/intensity of infusion related reactions.

For the production of the subcutaneous CD20 antibody (preferably Rituximab) formulation in accordance with the invention requires high antibody concentrations (approx. 120 mg/ml) in the final step of purification of the manufacturing process. Therefore an additional process step (ultrafiltration/diafiltration) is added to the conventional manufacturing process of the CD20 antibody, preferably Rituximab. The highly concentrated, stable pharmaceutical anti-CD20 antibody formulation in accordance with the present invention can also be provided as stabilized protein formulation which can reconstituted with a suitable diluent to generate a high anti-CD20 antibody concentration reconstituted formulation.

The CD20 antibody SC formulation in accordance with this invention is preferably used to treat cancer, preferably a CD20 expressing cancer.

The term "about" as used in the present patent specification is meant to specify that the specific value provided may vary to a certain extent, such as e.g. means that variations in the range of ±10%, preferably ±5%, most preferably ±2% are included in the given value.

Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

It is contemplated that the CD20 antibody SC formulation in accordance with this invention may also be used to treat various non-malignant diseases or disorders, such a include autoimmune disease as defined herein; endometriosis; scleroderma; restenosis; polyps such as colon polyps, nasal polyps or gastrointestinal polyps; fibroadenoma; respiratory disease; cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osier Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Preferred nonmalignant indications for therapy are as defined herein.

Where the indication is cancer, the patient may be treated with a combination of the antibody formulation, and a chemotherapeutic agent. The combined administration includes co-administration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the antibody formulation in accordance with the present invention. In this embodiment, the timing between at least one administration of the chemotherapeutic agent and at least one administration of the antibody formulation in accordance with the present invention is preferably approximately 1 month or less, and most preferably approximately 2 weeks or less. Alternatively, the chemotherapeutic agent and the antibody formulation in accordance with the present invention are administered concurrently to the patient, in a single formulation or separate formulations.

Treatment with the said antibody formulation will result in an improvement in the signs or symptoms of cancer or disease. For instance, where the disease being treated is cancer, such therapy may result in an improvement in survival (overall survival and/or progression free survival) and/or may result in an objective clinical response (partial or complete). Moreover, treatment with the combination of the chemotherapeutic agent and the antibody formulation may result in a synergistic or greater than additive, therapeutic benefit to the patient.

Preferably, the antibody in the formulation administered is a naked antibody. However, the antibody administered may be conjugated with a cytotoxic agent. Preferably, the immunoconjugate and/or antigen to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calioheamicins, ribonucleases and DNA endonucleases. The preferred immunoconjugates are Rituximab-maytansinoid immunoconjugates similarly to Trastuzumab-DM1 (T-DM1) as they are described in WO 2003/037992, more preferably the immunoconjugate T-MCC-DM1.

For subcutaneous delivery, the formulation may be administered via a suitable device, such as (but not limited to) a syringe; an injection device (e.g. the INJECT-EASE™ and GENJECT™ device); an infusion pump (such as e.g. Accu-Chek™); an injector pen (such as the GENPEN™; an needleless device (e.g. MEDDECTOR™ and BIOJECTOR™); or via a subcutaneous patch delivery system.

The amount of administration of said anti-CD20 antibody formulation for the prevention or treatment of disease, and the timing of administration will depend on the type (species, gender, age, weight, etc.) and condition of the patient being treated and the severity of the disease or condition being treated. Also important for the appropriate dose determination are the course of the disease, whether the antibody is administered for preventive or therapeutic purposes, the previous therapy, the patient's clinical history and his response to the antibody. The ultimate dose determination is at the discretion of the attending physician. The antibody is suitably administered to the patient at one time or over a series of treatments. Depending on the type and severity of the disease, about 1 µg/kg to 50 mg/kg (e.g. 0.1-20 mg/kg) of said anti-CD20 antibody is an initial candidate dosage for administration to the patient.

The preferred dosage of said anti-CD20 antibody will be in the range from about 0.05 mg/kg to about 30 mg/kg body weight. Thus, one or more doses of about 0.5 mg/kg, 2.0 mg/kg, 4.0 mg/kg, 10 mg/kg or 30 mg/kg (or any combination thereof) may be administered to the patient. Depending on the on the type (species, gender, age, weight, etc.) and condition of the patient and on the type of anti-CD20 antibody, the dosage of said first can differ from the dosage of the second anti-CD20 antibody. Such doses may be administered daily or intermittently, e.g. every third to six day or even every one to three weeks. An initial higher loading dose, followed by one or more lower doses may be administered. Based on clinical studies (see also Examples 3 and 4 for non-limiting exemplification for rituximab), the preferred dosage range is 300 mg/m$^2$ to 900 mg/m$^2$. More preferred, the preferred dosage range of said anti-CD20 antibody is about 375 mg/m$^2$ to about 800 mg/m$^2$. Preferred specific dosages of said anti-CD20 antibody are dosages of about 375 mg/m$^2$, about 625 mg/m$^2$ and about 800 mg/m$^2$. Also preferred are fixed doses of said anti-CD20 antibody.

In one embodiment, fixed dosages for B-cell lymphomas, preferably Non-Hodgkin's lymphoma, are as follows. Preferred are about 1200 mg to about 1800 mg of said anti-CD20 antibody per dose. More preferred are dosages selected from the group of about 1300 mg, about 1500 mg, about 1600 mg, and about 1700 mg of said anti-CD20 antibody per dose. Most preferred, the fixed dosage for B-cell lymphoma patients, preferably Non-Hodgkin's lymphoma patients, is about 1400 mg of said anti-CD20 antibody (e.g. Rituximab) per dose which may be administered according to various schedules including approximately every 2 months (including approximately every 8 weeks), approximately every 3 months (including approximately every 12 weeks), for about 2 years (or more), etc (see also Examples 3 and 4 for non-limiting exemplification for rituximab).

In another embodiment, fixed dosages for leukemia patients, preferably chronic lymphocytic leukemia (CLL) patients, are as follows. Preferred are about 1600 mg to about 2200 mg of said anti-CD20 antibody per dose. More preferred are dosages selected from the group of about 1700 mg, about 1800 mg, about 1900 mg, and about 2100 mg of said anti-CD20 antibody per dose. In one embodiment, the fixed dosage for leukemia patients, preferably CLL patients, is about 1870 mg of said anti-CD20 antibody (e.g. Rituximab) per dose.

In yet another embodiment, fixed dosages for patients with autoimmune disease, such as rheumatoid arthritis, multiple sclerosis, lupus nephritis, diabetes, ITP, and vasculitis are as follows. Preferred are about 1200 mg to about 2200 mg of said anti-CD20 antibody per dose, for example about 1500 mg of said anti-CD20 antibody (e.g. Rituximab) per dose.

If a chemotherapeutic agent is administered, it is usually administered at dosages known therefore, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The stable pharmaceutical formulation of the pharmaceutically active anti-CD20 antibody in accordance with the invention is preferably administered as subcutaneous injection, whereby the administration is preferably repeated several times with time intervals of 3 weeks (q3w). Most preferably the full volume of the injection fluid is administered within a time period of 1 to 10 minutes, preferably 2 to 6 minutes, most preferably 3±1 minutes. Most preferably, 2 ml/minute are administered, i.e. for example approx. 240 mg/min. For many patients where no other intravenous (IV) chemotherapeutic agents are given, such subcutaneous administration leads to increased patient convenience with the potential for self-administration at home. This leads to improved compliance and would reduce/eliminate costs associated with IV administration (viz., nursing costs for IV administration, rental of day-beds, patient travel etc). Subcutaneous administration in accordance with the present invention will most likely be associated with a reduced frequency and/or intensity of infusion-related reactions.

In a preferred embodiment, the medicament is useful for preventing or reducing metastasis or further dissemination in such a patient suffering from CD20 expressing cancer. The medicament is useful for increasing the duration of survival of such a patient, increasing the progression free survival of such a patient, increasing the duration of response, resulting in a statistically significant and clinically meaningful improvement of the treated patient as measured by the duration of survival, progression free survival, response rate or duration of response. In a preferred embodiment, the medicament is useful for increasing the response rate in a group of patients.

In the context of this invention, one or more additional other growth-inhibitory, cytotoxic, chemotherapeutic, anti-angiogenic, anti-cancer agents or cytokine(s), or compounds that enhance the effects of such agents may be used in the anti-CD20 antibody treatment of CD20 expressing cancer. Preferably the anti-CD20 antibody treatment is used without such additional cytotoxic, chemotherapeutic or anti-cancer agents, or compounds that enhance the effects of such agents.

Such agents include, for example: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6MP), 6-thiocguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and paclitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil. Preferably the anti-CD20 antibody treatment is used without such additional agents.

The use of the cytotoxic and anticancer agents described above as well as antiproliferative target-specific anticancer drug like protein kinase inhibitors in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, an effective amount of ionizing radiation may be carried out and/or a radiopharmaceutical may be used in addition to the anti-CD20 antibody treatment of CD20 expressing cancer. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Is also possible to label the antibody with such radioactive isotopes. Preferably the anti-CD20 antibody treatment is used without such ionizing radiation.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the CD20 antibody formulation of the invention is enhanced when combined with radiation, optionally with additional chemotherapeutic or anticancer agents. Parameters of adjuvant radiation therapies are, for example, contained in WO 99/60023.

Other therapeutic regimens may be combined with the antibody including, but not limited to a second (third, fourth, etc) chemotherapeutic agent(s) (in another word a "cocktail" of different chemotherapeutic agents); another monoclonal antibody; a growth inhibitory agent; a cytotoxic agent; a chemotherapeutic agent; an anti-angiogenic agent; and/or cytokine, etc.; or any suitable combination thereof.

In addition to the above therapeutic regimes, the patient may be subjected to surgical removal of cancer cells and/or radiation therapy.

In another embodiment of the invention, an article of manufacture is provided which contains the pharmaceutical formulation of the present invention and provides instructions for its use. This article of manufacture comprises a container. Suitable containers include, for example, bottles, vials (e.g. multiple or dual chamber vials), syringes (such as multiple or dual chamber syringes) and test tubes. The container may be formed from a variety of materials such as glass or plastic. The container holds the formulation and the label on, or associated with, the container may indicate directions for use. The container holding the formulation may be a multi-use vial, which allows for repeat administrations (e.g. from 2 to 6 administrations) of the reconstituted formulation. The article of manufacture may further include other materials desirable from a commercial and user standpoint, including other buffers, diluents, filters, needles, syringes, and package inserts with instructions for use.

The antibody which is formulated in accordance with the present invention is preferably essentially pure and desirably essentially homogeneous (i.e. free from contaminating proteins etc, whereby the hyaluronidase enzyme in the formulation in accordance of this invention is not to be considered to be a contaminating protein of the anti-CD20 monoclonal antibody in accordance of the present invention).

The invention will be more fully understood by reference to the following Examples. They should not, however, be construed as limiting the scope of the invention. All literature and patent citations are incorporated herein by reference.

EXAMPLES

The anti-CD20 formulations for subcutaneous administration according to the invention were developed based on the experimental results as provided below using the general preparatory and analytical methods and assays as outlined below.

Example 1

Preparation of Highly Concentrated Liquid Formulations

Rituximab is manufactured by techniques generally known from the production of recombinant proteins. A genetically engineered Chinese hamster ovary cell line (CHO) prepared as described in U.S. Pat. No. 7,381,560 is expanded in cell culture from a master cell bank. The Rituximab monoclonal antibody is harvested from the cell culture fluid and purified using immobilized Protein A affinity chromatography, cation exchange chromatography, a filtration step to remove viral contaminations, followed by anion exchange chromatography and an ultrafiltration/diafiltration step.

rHuPH20 is manufactured by techniques generally known from the production of recombinant proteins. The process begins with thawing of cells from the working cell bank (WCB) or master cell bank (MCB) and expansion through cell culture in a series of spinner flasks. The cell culture up to 6 liters is used to provide a continuous source of cells maintained under selective pressure with methotrexate. When expanded to approximately 36 liters the culture is transferred to a 400 liters bioreactor for a final batch volume of approximately 300 liters. The production bioreactor is operated in the fed-batch mode, with no selection pressure, and the duration of the production phase is approximately two weeks. rHuPH20 is secreted into the culture fluid. A 1000 liters bioreactor can also be used for a final batch volume of 500 liters. After completion of the production phase, the harvest is clarified by filtration, and is then treated with solvent/detergent to inactivate viruses. The protein is then purified by a series of four column chromatography processes to remove process and product related impurities. A viral filtration step is performed, and the filtered bulk is then concentrated, formulated into the final buffer: 10 mg/mL rHuPH20 in 20 mM L-histidine/HCl buffer, pH 6.5, 130 mM NaCl, 0.05% (w/v) polysorbate 80. The rHuPH20 bulk is stored below −70° C.

The other excipients of the formulation in accordance with the present invention are widely used in the practice and known to the person skilled in the art. There is therefore no need to be explained them here in detail.

Liquid drug product formulations for subcutaneous administration according to the invention were developed as follows.

For the preparation of the liquid formulations Rituximab was buffer exchanged against a diafiltration buffer containing the anticipated buffer composition and where required, concentrated by diafiltration to an antibody concentration of approx. 200 mg/ml. After completion of the diafiltration operation, the excipients (e.g. trehalose, rHuPH20, surfactant) were added as stock solutions to the antibody solution. Finally the protein concentration was adjusted with a buffer to the final Rituximab concentration of approx. 120 mg/ml.

All formulations were sterile-filtered through 0.22 µm low protein binding filters and aseptically filled into sterile 6 ml glass vials closed with ETFE (Copolymer of ethylene and tetrafluoroethylene)-coated rubber stoppers and alucrimp caps. The fill volume was approx. 3.0 ml. These formulations were stored at different climate conditions (5° C., 25° C. and 40° C.) for different intervals of time and stressed by shaking (1 week at a shaking frequency of 200 rpm at 5° C. and 25° C.) and freeze-thaw stress methods. The samples were analyzed before and after applying the stress tests by the following analytical methods:

1) UV spectrophotometry;
2) Size Exclusion Chromatography (SEC);
3) by Ion exchange chromatography (IEC);
4) by turbidity of the solution;
5) for visible particles; and
6) for rHuPH20 activity.

UV spectroscopy, used for determination of protein content, was performed on a Perkin Elmer λ35 UV spectrophotometer in a wavelength range from 240 nm to 400 nm. Neat protein samples were diluted to approx. 0.5 mg/ml with the corresponding formulation buffer. The protein concentration was calculated according to Equation 1.

$$\text{Protein content} = \frac{A(280) - A(320) \times \text{dil. factor}}{\varepsilon \langle cm^2/mg \rangle \times d \langle cm \rangle} \quad \text{Equation 1}$$

The UV light absorption at 280 nm was corrected for light scattering at 320 nm and multiplied with the dilution factor, which was determined from the weighed masses and densities of the neat sample and the dilution buffer. The numerator was divided by the product of the cuvette's path length d and the extinction coefficient ε.

Size Exclusion Chromatography (SEC) was used to detect soluble high molecular weight species (aggregates) and low molecular weight hydrolysis products (LMW) in the formulations. The method used a suitable HPLC instrument equipped with a UV detector (detection wave length 280 nm) and a TosoHaas TSK G3000SWXL column (7.8×300 mm). Intact monomer, aggregates and hydrolysis products were separated by an isocratic elution profile, using 0.2M di-potassium hydrogen phosphate, 025M potassium chloride, pH 7.0 with a flow rate of 0.5 ml/min, Ion Exchange Chromatography (IEC) was performed to detect chemical degradation products altering the net charge of Rituximab in the formulations. For this purpose Rituximab was digested with Papain. The method used a suitable HPLC instrument equipped with a UV detector (detection wavelength 280 nm) and a Polymer Labs PL-SCX 1000A analytical cation-exchange column. 10 mM MES, pH 6.0 and 10 mM MES, 0.2M sodium chloride, pH 6.0, were used as mobile phases A and B, respectively, with a flow rate of 1 ml/min.

For the determination of the turbidity, opalescence was measured in FTU (turbidity units) using a HACH 2100AN turbidimeter at room temperature.

Samples were analyzed for visible particles by using a Seidenader V90-T visual inspection instrument.

An in vitro enzyme assay of rHuPH20 as hyaluronidase was used as activity assay. The assay is based on the formation of an insoluble precipitate when hyaluronan (sodium hyaluronate) binds to a cationic precipitant. Enzyme activity was measured by incubating rHuPH20 with hyaluronan substrate and then precipitating the undigested hyaluronan with acidified serum albumin (horse serum). The turbidity was measured at a wavelength of 640 nm and the decrease in turbidity resulting from enzyme activity on the hyaluronan substrate is a measure of the enzyme activity. The procedure is run using a standard curve generated with dilutions of rHuPH20 assay reference standard, and sample activity is read from the curve.

The results of the stability testing for the Formulations A to J are provided in the tables below.

Compositions and Stability Data of Liquid Rituximab Drug Product Formulations According to this Invention Formulation A is a liquid formulation with the composition 120 mg/ml Rituximab, 20 mM L-histidine, 210 mM trehalose dihydrate, 10 mM methionine, 0.06% polysorbate 80, 2,000 U/ml rHuPH20, at pH 5.5.

| Storage temperature/ stress condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| — | Initial | 114 | 2.2 | 97.8 | 0.1 | 24 | 65 | 4.2 | Free from particles | 1970 |
| Shaking 5° C. | 1 week | 114 | 2.4 | 97.5 | 0.1 | n.d. | n.d. | 4.2 | Free from particles | 1760 |
| Shaking 25° C. | 1 week | 115 | 2.3 | 97.6 | 0.1 | n.d. | n.d. | 4.4 | Free from particles | 1676 |
| Freezing/ Thawing | 5 cycles | 114 | 2.4 | 97.5 | 0.1 | n.d. | n.d. | 4.4 | Free from particles | 2123 |
| 5° C. | 4 weeks | 114 | 2.2 | 97.8 | 0.1 | 25 | 65 | 4.7 | Free from particles | 1979 |
| | 13 weeks | 114 | 2.1 | 97.8 | 0.1 | 26 | 62 | 4.6 | Free from particles | 2219 |
| | 26 weeks | 114 | 2.1 | 97.8 | 0.2 | 25 | 63 | 4.4 | Free from particles | 2412 |

| Storage temperature/ stress condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| 25° C. | 4 weeks | 114 | 2.0 | 97.9 | 0.1 | 25 | 64 | 4.7 | Free from particles | 1975 |
| | 13 weeks | n.d. | 1.9 | 97.8 | 0.3 | 24 | 61 | 4.8 | Free from particles | 2215 |
| | 26 weeks | n.d. | 1.9 | 97.6 | 0.5 | 22 | 60 | 4.3 | Free from particles | 2409 |
| 40° C. | 4 weeks | 114 | 2.1 | 97.3 | 0.6 | 19 | 61 | 5.5 | Free from particles | n.d. |
| | 13 weeks | n.d. | 3.2 | 91.4 | 5.4 | 13 | 55 | 8.1 | Free from particles | n.d. | n.d. not determined

Formulation B is a liquid formulation with the composition 120 mg/ml Rituximab, 20 mM L-histidine, 210 mM trehalose dihydrate, 10 mM methionine, 0.06% polysorbate 80, 2,000 U/ml rHuPH20, at pH 6.1.

| Storage temperature/ stress condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| — | Initial | 117 | 2.3 | 97.7 | 0.1 | 25 | 63 | 7.1 | Free from particles | 2463 |
| Shaking 5° C. | 1 week | 116 | 2.2 | 97.7 | 0.1 | n.d. | n.d. | 7.2 | Free from particles | 2288 |
| Shaking 25° C. | 1 week | 118 | 2.1 | 97.8 | 0.1 | n.d. | n.d. | 6.9 | Free from particles | 2613 |
| Freezing/ Thawing | (5 cycles) | 116 | 2.3 | 97.7 | 0.1 | n.d. | n.d. | 6.6 | Essentially free from particles | 2259 |
| 5° C. | 4 weeks | 117 | 2.2 | 97.8 | 0.1 | 25 | 62 | 6.3 | Free from particles | 2485 |
| | 13 weeks | 114 | 2.3 | 97.6 | 0.1 | 25 | 62 | 6.3 | Free from particles | 2237 |
| | 26 weeks | 119 | 2.2 | 97.7 | 0.1 | 25 | 61 | 6.8 | Free from particles | 2344 |
| 25° C. | 4 weeks | n.d. | 2.0 | 97.9 | 0.1 | 25 | 62 | 6.6 | Free from particles | 2179 |
| | 13 weeks | n.d. | 2.1 | 97.7 | 0.2 | 24 | 61 | 6.3 | Free from particles | 2083 |
| | 26 weeks | n.d. | 2.1 | 96.2 | 1.8 | 23 | 60 | 6.9 | Free from particles | 2397 |
| 40° C. | 4 weeks | n.d. | 2.2 | 96.1 | 1.7 | 21 | 59 | 8.6 | Free from particles | n.d. |
| | 13 weeks | n.d. | 3.3 | 92.2 | 4.5 | 14 | 53 | 21.0 | Free from particles | n.d. | n.d. not determined

Formulation C is a liquid formulation with the composition 120 mg/ml Rituximab, 20 mM L-histidine, 210 mM trehalose dihydrate, 10 mM methionine, 0.06% polysorbate 80, 12,000 U/ml rHuPH20, at pH 5.5.

| Storage condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| — | Initial | 126 | 1.7 | 98.3 | 0.0 | 27 | 58 | 4.4 | Free from particles | 11963 |
| Shaking 5° C. | 1 week | 127 | 1.6 | 98.3 | 0.0 | n.d. | n.d. | 4.0 | Free from particles | 12083 |
| Shaking 25° C. | 1 week | 127 | 1.6 | 98.4 | 0.1 | n.d. | n.d. | 4.5 | Free from particles | 11150 |
| Freezing/ Thawing | (5 cycles) | 126 | 1.6 | 98.4 | 0.0 | n.d. | n.d. | 4.2 | Essentially free from particles | 11869 |
| 5° C. | 7 weeks | 124 | 1.5 | 98.5 | 0.0 | 26 | 62 | 5.0 | Free from particles | 12206 |

-continued

| Storage condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| | 19 weeks | 120 | 1.5 | 98.5 | 0.1 | 26 | 62 | 4.1 | Free from particles | 11945 |
| | 26 weeks | n.d. | n.d. | n.d. | n.d. | n.d. | n.d. | n.d. | Free from particles | n.d. |
| 25° C. | 7 weeks | n.d. | 1.5 | 97.8 | 0.7 | 25 | 63 | 5.8 | Free from particles | 12259 |
| | 19 weeks | n.d. | 1.5 | 97.3 | 1.2 | 24 | 61 | 4.8 | Free from particles | 13137 |
| | 26 weeks | n.d. | 1.8 | 96.6 | 1.6 | 24 | 60 | 4.4 | Free from particles | 12948 |
| 40° C. | 7 weeks | n.d. | 2.5 | 94.6 | 2.9 | 18 | 60 | 10.2 | Free from particles | n.d. |
| | 19 weeks | n.d. | 3.7 | 89.8 | 6.5 | 12 | 55 | 20.0 | Free from particles | n.d. | n.d. not determined

Formulation D is a liquid formulation with the composition 120 mg/ml Rituximab, 20 mM acetic acid, 210 mM trehalose dihydrate, 10 mM methionine, 0.06% polysorbate 20, 12,000 U/ml rHuPH20, at pH 5.5.

| Storage condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| — | Initial | 127 | 1.6 | 98.4 | 0.0 | 26 | 62 | 4.9 | Free from particles | 12619 |
| Shaking 5° C. | 1 week | 125 | 1.5 | 98.4 | 0.0 | n.d. | n.d. | 4.3 | Free from particles | 12507 |
| Shaking 25° C. | 1 week | 123 | 1.5 | 98.4 | 0.1 | n.d. | n.d. | 4.3 | Free from particles | 12923 |
| Freezing/Thawing | (5 cycles) | 124 | 1.5 | 98.4 | 0.0 | n.d. | n.d. | 4.4 | Essentially free from particles | 12394 |
| 5° C. | 7 weeks | 125 | 1.5 | 98.4 | 0.0 | 26 | 63 | 5.0 | Essentially free from particles | 10030 |
| | 19 weeks | 123 | 1.5 | 98.5 | 0.1 | 26 | 62 | 4.7 | Free from particles | 15324 |
| | 26 weeks | n.d. | n.d. | n.d. | n.d. | n.d. | n.d. | n.d. | Free from particles | n.d. |
| 25° C. | 7 weeks | n.d. | 1.6 | 97.7 | 0.7 | 25 | 62 | 4.9 | Free from particles | 13099 |
| | 19 weeks | n.d. | 1.6 | 97.2 | 1.2 | 24 | 61 | 5.1 | Free from particles | 13031 |
| | 26 weeks | n.d. | n.d. | n.d. | n.d. | n.d. | n.d. | n.d. | Free from particles | n.d. |
| 40° C. | 7 weeks | n.d. | 2.6 | 94.8 | 2.6 | 17 | 60 | 28.7 | Free from particles | n.d. |
| | 19 weeks | n.d. | 3.6 | 90.5 | 6.0 | 9 | 56 | 51.9 | Free from particles | n.d. | n.d. not determined

Formulation E is a liquid formulation with the composition 120 mg/ml Rituximab, 20 mM L-histidine, 210 mM trehalose dihydrate, 10 mM methionine, 0.06% polysorbate 20, 12,000 U/ml rHuPH20, at pH 5.5.

| Storage condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| — | Initial | 126 | 1.5 | 98.5 | 0.0 | 26 | 62 | 4.6 | Essentially free from particles | 12231 |
| Shaking 5° C. | 1 week | 128 | 1.5 | 98.5 | 0.0 | n.d. | n.d. | 4.4 | Essentially free from particles | 12524 |
| Shaking 25° C. | 1 week | 127 | 1.5 | 98.5 | 0.1 | n.d. | n.d. | 4.2 | Free from particles | 11438 |

-continued

| Storage condition | Storage Time | Protein concentration (mg/ml) | Size Exclusion-HPLC ||| Ion Exchange-HPLC || Turbidity (FTU) | Visible particles | Enzyme activity (U/ml) |
|---|---|---|---|---|---|---|---|---|---|---|
| | | | HMW (%) | Monomer (%) | LMW (%) | Fc-Lys (%) | Fab pE/Q (%) | | | |
| Freezing/ Thawing | (5 cycles) | 127 | 1.5 | 98.5 | 0.0 | n.d. | n.d. | 4.3 | Free from particles | 14440 |
| 5° C. | 7 weeks | 125 | 1.5 | 98.5 | 0.0 | 26 | 62 | 4.7 | Free from particles | 12824 |
| | 19 weeks | 125 | 1.5 | 98.5 | 0.1 | 26 | 62 | 4.5 | Free from particles | 13891 |
| | 26 weeks | n.d. | n.d. | n.d. | n.d. | n.d. | n.d. | n.d. | Free from particles | n.d. |
| 25° C. | 7 weeks | n.d. | 1.5 | 97.8 | 0.7 | 25 | 62 | 4.3 | Free from particles | 13540 |
| | 19 weeks | n.d. | 1.5 | 97.4 | 1.1 | 24 | 61 | 4.6 | Free from particles | 11243 |
| | 26 weeks | n.d. | n.d. | n.d. | n.d. | n.d. | n.d. | n.d. | Free from particles | n.d. |
| 40° C. | 7 weeks | n.d. | 2.5 | 94.6 | 2.9 | 18 | 60 | 10.6 | Free from particles | n.d. |
| | 19 weeks | n.d. | 3.9 | 89.6 | 6.5 | 12 | 55 | 22.7 | Free from particles | n.d. | n.d. not determined

Formulation F is a liquid formulation with the composition 120 mg/ml Rituximab, 20 mM L-histidine, 120 mM sodium chloride, 10 mM methionine, 0.02% polysorbate 80, 12,000 U/ml rHuPH20, at pH 5.5.

| Storage condition | Storage Time | Protein concentration (mg/ml) | Size Exclusion-HPLC ||| Ion Exchange-HPLC |||| Turbidity (FTU) | Visible particles | Enzyme activity (U/ml) |
|---|---|---|---|---|---|---|---|---|---|---|---|
| | | | HMW (%) | Monomer (%) | LMW (%) | Fab NS clips a + b (%) | Fc-Lys (%) | Fab pE/Q (%) | | | |
| — | Initial | 124 | 1.6 | 98.3 | 0.0 | 3 | 26 | 62 | 28.7 | Free from particles | 12034 |
| Shaking 5° C. | 1 week | 127 | 1.6 | 98.4 | 0.0 | n.d. | n.d. | n.d. | 31.0 | Free from particles | 12083 |
| Shaking 25° C. | 1 week | 125 | 2.4 | 97.5 | 0.1 | n.d. | n.d. | n.d. | 31.1 | Free from particles | 11150 |
| Freezing/ Thawing | (5 cycles) | 125 | 1.9 | 98.1 | 0.0 | n.d. | n.d. | n.d. | 30.4 | Free from particles | 11869 |
| 5° C. | 7 weeks | 122 | 1.6 | 98.4 | 0.0 | 3 | 25 | 63 | 31.4 | Free from particles | 10368 |
| | 19 weeks | 118 | 1.5 | 98.4 | 0.1 | 3 | 26 | 62 | 31.8 | Free from particles | 11654 |
| | 26 weeks | n.d. | n.d. | n.d. | n.d. | n.d. | n.d. | n.d. | n.d. | Free from particles | n.d. |
| 25° C. | 7 weeks | n.d. | 1.7 | 97.6 | 0.7 | 3 | 25 | 63 | 31.1 | Free from particles | 13853 |
| | 19 weeks | n.d. | 1.7 | 97.1 | 1.2 | 3 | 24 | 61 | 31.6 | Free from particles | 12556 |
| | 26 weeks | n.d. | n.d. | n.d. | n.d. | n.d. | n.d. | n.d. | n.d. | Free from particles | n.d. |
| 40° C. | 7 weeks | n.d. | 2.9 | 94.1 | 3.1 | 5 | 19 | 59 | 87.0 | Free from particles | n.d. |
| | 19 weeks | n.d. | 4.3 | 88.8 | 6.9 | 6 | 13 | 55 | 211.0 | Free from particles | n.d. | n.d. not determined

Formulation G is a liquid formulation with the composition 120 mg/ml Rituximab, 20 mM citric acid, 120 mM sodium chloride, 10 mM methionine, 0.02% polysorbate 80, 12,000 U/ml rHuPH20, at pH 6.5.

|  |  |  |  |  |  | Ion Exchange-HPLC | | |  |  |  |
|---|---|---|---|---|---|---|---|---|---|---|---|
|  |  | Protein | Size Exclusion-HPLC | | | Fab NS | | |  |  | Enzyme |
| Storage condition | Storage Time | concentration (mg/ml) | HMW (%) | Monomer (%) | LMW (%) | clips a + b (%) | Fc-Lys (%) | Fab pE/Q (%) | Turbidity (FTU) | Visible particles | activity (U/ml) |
| — | Initial | 126 | 1.8 | 98.1 | 0.0 | 4 | 26 | 62 | 40.3 | Free from particles | 10808 |
| Shaking 5° C. | 1 week | 122 | 1.8 | 98.2 | 0.0 | n.d. | n.d. | n.d. | 35.6 | Free from particles | 9324 |
| Shaking 25° C. | 1 week | 125 | 2.3 | 97.7 | 0.1 | n.d. | n.d. | n.d. | 35.7 | Free from particles | n.a. |
| Freezing/Thawing | (5 cycles) | 126 | 1.9 | 98.1 | 0.0 | n.d. | n.d. | n.d. | 34.5 | Free from particles | 11270 |
| 5° C. | 7 weeks | 124 | 1.8 | 98.2 | 0.0 | 3 | 24 | 63 | 38.5 | Essentially free from particles | 12854 |
|  | 19 weeks | 118 | 1.7 | 98.2 | 0.1 | 3 | 26 | 62 | 37.6 | Free from particles | 11202 |
|  | 26 weeks | n.d. | n.d. | n.d. | n.d. | n.d. | n.d. | n.d. |  | Free from particles | n.d |
| 25° C. | 7 weeks | n.d. | 1.9 | 97.4 | 0.7 | 2 | 24 | 63 | 40.2 | Essentially free from particles | 11645 |
|  | 19 weeks | n.d. | 2.1 | 96.9 | 1.1 | 3 | 24 | 60 | 36.9 | Free from particles | 14233 |
|  | 26 weeks | n.d. | n.d. | n.d. | n.d. | n.d. | n.d. | n.d. |  | Free from particles | n.d. |
| 40° C. | 7 weeks | n.d. | 3.1 | 94.3 | 2.6 | 5 | 19 | 58 | 101.0 | Essentially free from particles | n.d. |
|  | 19 weeks | n.d. | 4.8 | 89.4 | 5.8 | 7 | 12 | 52 | 385.0 | Free from particles | n.d. | n.d. not determined

Formulation H is a liquid formulation with the composition 120 mg/ml Rituximab, 20 mM citric acid, 210 mM trehalose dihydrate, 10 mM methionine, 0.06% polysorbate 80, 12,000 U/ml rHuPH20, at pH 6.5.

|  |  |  |  |  |  | Ion Exchange-HPLC | | |  |  |  |
|---|---|---|---|---|---|---|---|---|---|---|---|
|  |  | Protein | Size Exclusion-HPLC | | | Fab NS | | |  |  | Enzyme |
| Storage condition | Storage Time | concentration (mg/ml) | HMW (%) | Monomer (%) | LMW (%) | clips a + b (%) | Fc-Lys (%) | Fab pE/Q (%) | Turbidity (FTU) | Visible particles | activity (U/ml) |
| — | Initial | 127 | 2.0 | 98.0 | 0.0 | 3 | 26 | 62 | 33.4 | Free from particles | 11951 |
| Shaking 5° C. | 1 week | 128 | 1.9 | 98.1 | 0.0 | n.d. | n.d. | n.d. | 30.3 | Free from particles | 10936 |
| Shaking 25° C. | 1 week | 127 | 1.9 | 98.0 | 0.1 | n.d. | n.d. | n.d. | 29.7 | Free from particles | 12595 |
| Freezing/Thawing | (5 cycles) | 127 | 1.9 | 98.1 | 0.0 | n.d. | n.d. | n.d. | 32.0 | Free from particles | 11442 |
| 5° C. | 7 weeks | 124 | 1.8 | 98.2 | 0.0 | 3 | 24 | 63 | 33.8 | Free from particles | 11723 |
|  | 19 weeks | 122 | 1.7 | 98.2 | 0.1 | 3 | 26 | 62 | 30.8 | Free from particles | 12180 |
|  | 26 weeks | n.d. | n.d. | n.d. | n.d. | n.d. | n.d. | n.d. | n.d. | Free from particles | n.d. |
| 25° C. | 7 weeks | n.d. | 2.0 | 97.3 | 0.7 | 3 | 25 | 62 | 30.8 | Free from particles | 12328 |
|  | 19 weeks | n.d. | 2.1 | 96.9 | 1.1 | 4 | 24 | 60 | 31.4 | Free from particles | 12017 |
|  | 26 weeks | n.d. | n.d. | n.d. | n.d. | n.d. | n.d. | n.d. | n.d. | Free from particles | n.d. |
| 40° C. | 7 weeks | n.d. | n.d. | n.d. | n.d. | 5 | 20 | 58 | 84.8 | Free from particles | n d. |
|  | 19 weeks | n.d. | n.d. | n.d. | n.d. | 7 | 11 | 50 | 295.0 | Free from particles | n.d. | n.d. not determined

Formulation I is a liquid formulation with the composition 120 mg/ml Rituximab, 20 mM L-histidine, 120 mM sodium chloride, 10 mM methionine, 0.04% polysorbate 80, 12,000 U/ml rHuPH20, at pH 6.0.

| Storage condition | Storage Time | Protein concentration (mg/ml) | Size Exclusion-HPLC | | | Ion Exchange-HPLC | | | Turbidity (FTU) | Visible particles | Enzyme activity (U/ml) |
|---|---|---|---|---|---|---|---|---|---|---|---|
| | | | HMW (%) | Monomer (%) | LMW (%) | Fab NS clips a + b (%) | Fc-Lys (%) | Fab pE/Q (%) | | | |
| — | Initial | 123 | 1.7 | 98.3 | 0.0 | 3 | 25 | 62 | 34.0 | Free from particles | 11022 |
| Shaking 5° C. | 1 week | 125 | 1.6 | 98.3 | 0.0 | n.d. | n.d. | n.d. | 33.3 | Free from particles | 12231 |
| Shaking 25° C. | 1 week | 124 | 1.7 | 98.3 | 0.1 | n.d. | n.d. | n.d. | 32.1 | Free from particles | 8371 |
| Freezing/Thawing | (5 cycles) | 123 | 1.8 | 98.1 | 0.0 | n.d. | n.d. | n.d. | 32.9 | Free from particles | 12058 |
| 5° C. | 7 weeks | 122 | 1.6 | 98.4 | 0.0 | 3 | 25 | 62 | 33.5 | Free from particles | 11108 |
| | 19 weeks | 119 | 1.6 | 98.4 | 0.1 | 3 | 26 | 62 | 34.4 | Free from particles | 11548 |
| | 26 weeks | n.d. | n.d. | n.d. | n.d. | n.d. | n.d. | n.d. | n.d. | Free from particles | n.d. |
| 25° C. | 7 weeks | n.d. | 1.7 | 97.7 | 0.6 | 3 | 25 | 62 | 34.8 | Free from particles | 12679 |
| | 19 weeks | n.d. | 1.8 | 97.2 | 1.1 | 4 | 24 | 60 | 34.6 | Free from particles | 13252 |
| | 26 weeks | n.d. | n.d. | n.d. | n.d. | n.d. | n.d. | n.d. | n.d. | Free from particles | n.d. |
| 40° C. | 7 weeks | n.d. | 2.5 | 94.9 | 2.6 | 5 | 20 | 58 | 88.1 | Free from particles | n.d. |
| | 19 weeks | n.d. | 3.7 | 90.4 | 5.9 | 7 | 14 | 53 | 292.0 | Free from particles | n.d. | n.d. not determined

Formulation J is a liquid formulation with the composition 25 mg/ml GA101 (huMAb<CD20>), 20 mM L-histidine, 240 mM trehalose dihydrate, 0.02% poloxamer 188, 2,000 U/ml rHuPH20, at pH 6.0.

All formulations were sterile-filtered through 0.22 μm low protein binding filters and aseptically filled into sterile 3 ml glass vials stoppered with fluoro-resin laminated butyl rubber stoppers and capped with aluminum/plastic flip-off seals.

| Storage temperature/ stress condition | Storage Time | Protein concentration (mg/ml) | Size Exclusion-HPLC | | | Ion Exchange-HPLC | | Turbidity (FTU) | Visible particles | Enzyme activity (U/ml) |
|---|---|---|---|---|---|---|---|---|---|---|
| | | | HMW (%) | Monomer (%) | LMW (%) | Acidic region (%) | Main Peak (%) | | | |
| — | Initial | 25.1 | 0.6 | 98.5 | 0.9 | 18.5 | 68.6 | 6.0 | Free from particles | 1833 |
| −20° C. | 26 weeks | 26.2 | 0.6 | 98.6 | 0.8 | 18.7 | 68.3 | 5.8 | Free from particles | 2078 |
| 5° C. | 26 weeks | 25.7 | 0.7 | 98.4 | 0.9 | 19.1 | 67.9 | 5.6 | Free from particles | 1380 |
| 25° C. | 26 weeks | 25.9 | 0.9 | 97.3 | 1.9 | 26.7 | 60.8 | 6.0 | Free from particles | 978 |
| 40° C. | 26 weeks | 26.1 | 3.0 | 86.8 | 9.7 | 40.9 | 19.5 | 7.2 | Essentially free from particles | <limit of quantification | n.d. not determined

Example 2

Preparation of Humanized 2H7 anti-CD20 Liquid Formulations

For the preparation of the liquid formulations, recombinant humanized 2H7 anti-CD20 antibody (2H7.v16 as disclosed in WO 2006/084264) was buffer exchanged against a diafiltration buffer containing the anticipated buffer composition and where required, concentrated to an antibody concentration of approx. 60 and 120 mg/ml. After achieving the target concentration, the excipients (e.g. trehalose, rHuPH20, polysorbate 20) were then added as stock solutions to the antibody solution. Finally the protein concentration was adjusted with the final formulation buffer to a humanized 2H7 concentration of approx. 30, 50, and 100 mg/ml.

The fill volume was approx. 1.2 ml. These formulations were stored at different temperatures (5° C., 25° C. and 40° C.) for different intervals of time. The samples were analyzed at each stability time point by the following analytical methods:

1) UV spectrophotometry
2) Size exclusion chromatography (SEC);
3) Ion exchange chromatography (IEC);
4) Complement dependent cytotoxicity (CDC) assay for humanized 2H7 activity
5) Turbidometric assay for rHuPH20 activity 1). Protein concentration was determined by ultraviolet absorption spectroscopy using an Agilent 8453 spectrophotometer in a wavelength range from 240 nm to 400 nm. Samples were gravimetrically diluted to approx. 0.5 mg/ml with the corresponding formulation buffer. The protein concentrations were calculated using Equation 1:

$$\text{Protein concentration} = ((A_{max} - A_{320}) \times DF)/(\varepsilon(\text{cm}^2/\text{mg}) \times d(\text{cm})) \quad \text{(Equation 1)}$$

wherein DF is the dilution factor, d is the cuvette path length and $\varepsilon$ is the extinction coefficient, which is 1.75 (cm$^2$/mg$^{-1}$) for 2H7 at $A_{max}$. The UV light absorption at $A_{max}$ (typically 278 to 280 nm) was corrected for light scattering at 320 nm and multiplied with the dilution factor, which was determined from the weighed masses and densities of the neat sample and the dilution buffer. The numerator was divided by the product of the cuvette's path length d and the extinction coefficient $\varepsilon$.

2). Size Exclusion Chromatography (SEC) was used to detect soluble high molecular weight species (aggregates) and low molecular weight hydrolysis products (fragments) in the formulations. SEC was carried out on an Agilent Technologies, Inc. 1100 series HPLC equipped with a UV detector (detection wave length 280 nm) and a TSK G3000SWXL column (7.8×300 mm). Intact monomer, aggregates and hydrolysis products were separated by an isocratic elution profile, using 0.20M potassium phosphate and 0.25M potassium chloride at pH 6.2 with a flow rate of 0.3 ml/min.

3). Ion Exchange Chromatography (IEC) was performed to detect chemical degradation products that alter the net charge of the anti-CD20 antibody in the formulations. For this purpose, the anti-CD20 antibody is incubated with Carboxypeptidase B to catalyze the hydrolysis of basic amino acids. Ion exchange chromatography was carried out on an Agilent Technologies, Inc. 1100 series HPLC with a UV detector (detection wavelength 280 nm) and a Dionex ProPac WCX-10 (4×250 mm) column. Acidic and basic variants were separated using a linear gradient of 25 mM potassium phosphate at pH 6.9 (mobile phase A) and 120 mM potassium chloride dissolved in 25 mM potassium phosphate (mobile phase B) with a flow rate of 0.5 mL/min.

4). The complement-dependent cytotoxicity assay (CDC) assay was performed to determine the in vitro activity of the anti-CD20 antibody. The complement dependent cytotoxicity (CDC) potency assay is used to measure the ability of the antibody to lyse human B lymphoblastoid (WIL2-S) cells in the presence of human complement. The assay is performed in 96 well tissue culture microtiter plates. In this assay, varying concentrations of the anti-CD20 antibody reference material, control, or sample(s) diluted in assay diluent are incubated with WIL2-S cells (50,000 cells/well) in the presence of a fixed amount of human complement. The plate is incubated at 37° C./5% CO2 in a humidified incubator for 1 to 2 hours. At the end of the incubation period, 50 µL of the redox dye, ALAMARBLUE™ is added to each well and the plate is incubated for 15 to 26 hours. ALAMARBLUE™ is a redox dye that fluoresces at an excitation wavelength of 530 nm and an emission wavelength of 590 nm when reduced by live cells. Therefore, the changes in color and fluorescence are proportional to the number of viable cells. The results, expressed in relative fluorescence units (RFU), are plotted against the anti-CD20 antibody concentrations and a parallel line program is used to estimate the activity of anti-CD20 antibody samples relative to the reference material.

5). A turbidimetric assay was used to determine hyaluronidase activity and enzyme concentration. This method is based on the formation of an insoluble precipitate when hyaluronic acid binds with acidified serum albumin. Briefly, a dilution series of the rhuPH20 hyaluronidase (Halozyme, Inc.) working reference standard ranging from 2.5 U/ml to 0.25 U/ml is prepared in enzyme diluent (70 mM NaCl, 25 mM PIPES, pH 5.5, 0.66 mg/ml gelatin hydrolysate, 0.1% human serum albumin). The test samples are diluted to a final concentration of 1.5 U/ml in enzyme diluent. 30 µl of the standard and sample dilutions are transferred into a "black clear bottom" 96-well plate (Nunc). The plate is then covered and pre-warmed for 5 minutes at 37° C. The reaction is then initiated by adding 30 µL of pre-warmed 0.25 mg/ml hyaluronic acid substrate solution (70 mM NaCl, 25 mM PIPES, pH 5.5, 0.25 mg/ml dried sodium hyaluronate, Lifecore Biomedical). The plate is shaken briefly and incubated for 10 minutes at 37° C. After this incubation step the reaction is stopped by adding 240 µL of serum working solution (2.5% horse serum, 500 mM potassium acetate, pH 4.25). After a 30 minute development period at room temperature the turbidity of the reaction is measured at a wavelength 640 nm on a microplate reader. The decrease in turbidity resulting from enzyme activity on the hyaluronic acid substrate is a measure of the hyaluronidase activity. The sample activity is determined relative to the calibration curve generated with the dilutions of the rhuPH20 working reference standard.

The results obtained with the various humanized 2H7 antibody formulations are shown in the following tables:

Formulation K is a liquid formulation with the composition 30 mg/ml humanized 2H7, 30 mM sodium acetate, 8% trehalose dihydrate, 0.02% polysorbate 20, 0 U/ml of rhuPH20 at pH 5.3.

| Storage temperature | Storage Time | Protein concentration (mg/ml) | Size Exclusion-HPLC | | | Ion Exchange-HPLC | | CDC Potency | Enzyme |
|---|---|---|---|---|---|---|---|---|---|
| | | | HMW (%) | Monomer (%) | LMW (%) | % Acidic Variant | % Main Peak | (% Specific Activity) | activity (U/ml) |
| — | Initial | 32 | 0.9 | 98.9 | 0.2 | 27.1 | 67.5 | 103 | ND |
| 5° C. | 12 weeks | ND | 0.8 | 98.1 | 1.1 | 27.8 | 65.9 | 110 | ND |
| | 24 weeks | ND | 0.8 | 98.1 | 1.1 | 25.6 | 68.1 | 89 | ND |
| | 36 weeks | ND | 0.9 | 98.6 | 0.5 | 27.0 | 68.3 | 97 | ND |
| | 48 weeks | ND | 1.0 | 97.4 | 1.6 | 25.9 | 68.3 | 96 | ND |
| | 72 weeks | ND | 0.9 | 97.9 | 1.2 | 25.2 | 68.2 | 109 | ND |
| | 96 weeks | ND | 0.9 | 97.8 | 1.3 | 28.1 | 66.1 | 96 | ND |
| 25° C. | 4 weeks | ND | 0.7 | 98.0 | 1.2 | 29.5 | 64.7 | ND | ND |
| | 8 weeks | ND | 0.8 | 97.7 | 1.5 | 32.5 | 61.9 | ND | ND |
| | 12 weeks | ND | 0.8 | 97.4 | 1.8 | 35.0 | 59.1 | 83 | ND |
| | 24 weeks | ND | 1.0 | 96.8 | 2.2 | 40.9 | 52.1 | ND | ND |
| 40° C. | 2 weeks | ND | 0.7 | 97.8 | 1.6 | 36.0 | 57.7 | ND | ND |
| | 4 weeks | ND | 0.8 | 96.6 | 2.5 | 45.1 | 47.4 | ND | ND |
| | 8 weeks | ND | 1.0 | 94.9 | 4.1 | 60.3 | 33.3 | ND | ND |

*ND not determined

Formulation L is a liquid formulation with the composition 30 mg/ml humanized 2H7, 30 mM sodium acetate, 8% trehalose dihydrate, 0.02% polysorbate 20, 1500 U/ml of rhuPH20 at pH 5.3.

| Storage temperature | Storage Time | Protein concentration (mg/ml) | Size Exclusion-HPLC | | | Ion Exchange-HPLC | | CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| — | Initial | 32 | 0.9 | 98.9 | 0.2 | 27.1 | 67.4 | 114 | 1309 |
| 5° C. | 12 weeks | ND | 0.8 | 97.9 | 1.3 | 27.6 | 65.7 | 110 | 1520 |
| | 24 weeks | ND | 0.8 | 98.1 | 1.2 | 26.1 | 67.1 | 82 | 1112 |
| | 36 weeks | ND | 0.9 | 97.3 | 1.8 | 27.0 | 67.9 | 98 | 1166 |
| | 48 weeks | ND | 0.9 | 97.3 | 1.8 | 26.2 | 67.9 | 100 | 1620 |
| | 72 weeks | ND | 0.9 | 97.9 | 1.3 | 26.0 | 68.2 | 97 | ND |
| | 96 weeks | ND | 0.9 | 97.8 | 1.3 | 28.1 | 66.0 | 96 | ND |
| 25° C. | 4 weeks | ND | 0.7 | 98.0 | 1.3 | 29.5 | 64.7 | ND | 1147 |
| | 8 weeks | ND | 0.8 | 97.8 | 1.4 | 32.1 | 61.9 | ND | 847 |
| | 12 weeks | ND | 0.8 | 97.3 | 1.9 | 35.1 | 59.3 | 89 | 892 |
| | 24 weeks | ND | 1.0 | 96.8 | 2.2 | 41.3 | 51.9 | ND | 777 |
| 40° C. | 2 weeks | ND | 0.8 | 97.6 | 1.6 | 35.3 | 57.4 | ND | ND |
| | 4 weeks | ND | 0.8 | 96.7 | 2.4 | 45.2 | 46.9 | ND | ND |
| | 8 weeks | ND | 1.0 | 95.0 | 4.0 | 59.8 | 34.3 | ND | ND |

*ND not determined

Formulation M is a liquid formulation with the composition 30 mg/ml humanized 2H7, 30 mM sodium acetate, 8% trehalose dihydrate, 0.02% polysorbate 20, 12,000 U/ml of rhuPH20 at pH 5.3.

| Storage temperature | Storage Time | Protein concentration (mg/ml) | Size Exclusion-HPLC | | | Ion Exchange-HPLC | | CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| — | Initial | 33 | 0.9 | 98.9 | 0.2 | 27.2 | 67.4 | 103 | 10584 |
| 5° C. | 12 weeks | ND | 0.8 | 97.7 | 1.6 | 26.5 | 66.8 | 111 | 8864 |
| | 24 weeks | ND | 0.8 | 97.8 | 1.4 | 25.8 | 68.1 | 85 | 14319 |
| | 36 weeks | ND | 0.8 | 97.5 | 1.7 | 27.1 | 68.0 | 96 | 11408 |
| | 48 weeks | ND | 0.9 | 96.7 | 2.4 | 26.2 | 67.9 | 95 | 13817 |
| | 72 weeks | ND | 0.9 | 97.6 | 1.6 | 26.4 | 68.0 | 98 | ND |
| | 96 weeks | ND | 0.9 | 97.4 | 1.6 | 28.3 | 65.8 | 108 | ND |
| 25° C. | 4 weeks | ND | 0.8 | 97.7 | 1.5 | 29.6 | 64.7 | ND | 13464 |
| | 8 weeks | ND | 0.8 | 97.4 | 1.7 | 32.1 | 61.9 | ND | 10975 |
| | 12 weeks | ND | 0.9 | 97.0 | 2.1 | 35.4 | 58.7 | 92 | 10394 |
| | 24 weeks | ND | 1.0 | 96.5 | 2.5 | 41.0 | 51.8 | ND | 819 |
| 40° C. | 2 weeks | ND | 1.1 | 97.3 | 1.6 | 35.7 | 57.2 | ND | ND |
| | 4 weeks | ND | 0.8 | 96.6 | 2.5 | 45.5 | 47.5 | ND | ND |
| | 8 weeks | ND | 1.0 | 94.9 | 4.1 | 59.9 | 33.3 | ND | ND |

*ND not determined

Formulation N is a liquid formulation with the composition 50 mg/ml humanized 2H7, 30 mM sodium acetate, 8% trehalose dihydrate, 0.02% polysorbate 20, 0 U/ml of rhuPH20 at pH 5.3.

| Storage temperature | Storage Time | Protein concentration (mg/ml) | Size Exclusion-HPLC | | | Ion Exchange-HPLC | | CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| — | Initial | 50 | 0.9 | 98.9 | 0.2 | 27.0 | 67.6 | 107 | ND |
| 5° C. | 12 weeks | ND | 0.9 | 98.1 | 1.0 | 26.9 | 66.6 | 86 | ND |
| | 24 weeks | ND | 0.9 | 97.9 | 1.1 | 25.8 | 67.7 | 88 | ND |
| | 36 weeks | ND | 1.0 | 97.9 | 1.1 | 27.1 | 68.5 | 92 | ND |
| | 48 weeks | ND | 1.0 | 97.8 | 1.2 | 26.2 | 67.8 | 95 | ND |
| | 72 weeks | ND | 1.0 | 97.8 | 1.2 | 26.5 | 67.9 | 101 | ND |
| | 96 weeks | ND | 1.1 | 97.6 | 1.3 | 28.4 | 65.8 | 98 | ND |
| 25° C. | 4 weeks | ND | 0.9 | 97.9 | 1.2 | 29.5 | 64.9 | ND | ND |
| | 8 weeks | ND | 0.9 | 97.6 | 1.5 | 32.1 | 61.8 | ND | ND |
| | 12 weeks | ND | 1.0 | 97.4 | 1.6 | 35.3 | 58.9 | 86 | ND |
| | 24 weeks | ND | 0.9 | 97.9 | 1.1 | 40.0 | 52.8 | ND | ND |

-continued

| Storage temperature | Storage Time | Protein concentration (mg/ml) | Size Exclusion-HPLC ||| Ion Exchange-HPLC || CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| 40° C. | 2 weeks | ND | 0.9 | 97.5 | 1.6 | 35.3 | 56.9 | ND | ND |
| | 4 weeks | ND | 1.1 | 96.2 | 2.7 | 45.2 | 47.8 | ND | ND |
| | 8 weeks | ND | 1.4 | 94.1 | 4.4 | 59.7 | 32.9 | ND | ND |

*ND not determined

Formulation O is a liquid formulation with the composition 50 mg/ml humanized 2H7, 30 mM sodium acetate, 8% trehalose dihydrate, 0.02% polysorbate 20, 1500 U/ml of rhuPH20 at pH 5.3.

| Storage temperature | Storage Time | Protein concentration (mg/ml) | Size Exclusion-HPLC ||| Ion Exchange-HPLC || CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| — | Initial | 51 | 0.9 | 98.9 | 0.2 | 27.1 | 67.4 | 116 | 1537 |
| 5° C. | 12 weeks | ND | 0.9 | 97.8 | 1.3 | 25.8 | 67.4 | 109 | 1454 |
| | 24 weeks | ND | 0.9 | 97.9 | 1.2 | 26.0 | 67.7 | 84 | 1372 |
| | 36 weeks | ND | 1.0 | 97.5 | 1.5 | 27.7 | 67.3 | 93 | 1432 |
| | 48 weeks | ND | 1.1 | 97.0 | 2.0 | 26.0 | 68.4 | 102 | 1356 |
| | 72 weeks | ND | 1.1 | 97.6 | 1.4 | 26.5 | 68.0 | 97 | ND |
| | 96 weeks | ND | 1.2 | 97.6 | 1.3 | 28.2 | 65.9 | 104 | ND |
| 25° C. | 4 weeks | ND | 0.9 | 97.9 | 1.3 | 29.7 | 64.6 | ND | 1269 |
| | 8 weeks | ND | 0.9 | 97.4 | 1.6 | 32.1 | 62.0 | ND | 966 |
| | 12 weeks | ND | 1.0 | 97.5 | 1.5 | 35.2 | 58.9 | 89 | 1002 |
| | 24 weeks | ND | 1.3 | 96.5 | 2.2 | 40.5 | 52.2 | ND | ND |
| 40° C. | 2 weeks | ND | 0.9 | 97.5 | 1.6 | 35.9 | 56.1 | ND | ND |
| | 4 weeks | ND | 1.1 | 96.3 | 2.6 | 46.5 | 45.7 | ND | ND |
| | 8 weeks | ND | 1.4 | 94.6 | 4.0 | 60.5 | 31.9 | ND | ND |

*ND not determined

Formulation P is a liquid formulation with the composition 50 mg/ml humanized 2H7, 30 mM sodium acetate, 8% trehalose dihydrate, 0.02% polysorbate 20, 12,000 U/ml of rhuPH20 at pH 5.3.

| Storage temperature | Storage Time | Protein concentration (mg/ml) | Size Exclusion-HPLC ||| Ion Exchange-HPLC || CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| — | Initial | 52 | 0.9 | 98.9 | 0.2 | 27.2 | 67.4 | 110 | 9932 |
| 5° C. | 12 weeks | ND | 0.9 | 97.7 | 1.4 | 26.8 | 67.6 | 102 | 9668 |
| | 24 weeks | ND | 0.9 | 97.7 | 1.4 | 25.7 | 68.2 | ND | 11292 |
| | 36 weeks | ND | 1.0 | 97.5 | 1.5 | 27.5 | 67.0 | 96 | 15469 |
| | 48 weeks | ND | 1.1 | 97.4 | 1.6 | 26.1 | 68.2 | 100 | 10832 |
| | 72 weeks | ND | 1.0 | 97.7 | 1.3 | 26.3 | 68.0 | 106 | ND |
| | 96 weeks | ND | 1.2 | 97.4 | 1.5 | 29.3 | 64.8 | 100 | ND |
| 25° C. | 4 weeks | ND | 0.9 | 97.6 | 1.5 | 29.7 | 64.6 | ND | 11765 |
| | 8 weeks | ND | 1.0 | 97.6 | 1.4 | 32.3 | 61.9 | ND | 11594 |
| | 12 weeks | ND | 1.1 | 97.1 | 1.8 | 35.4 | 58.8 | 86 | 10119 |
| | 24 weeks | ND | 1.2 | 96.4 | 2.4 | 41.1 | 51.8 | ND | 8960 |
| 40° C. | 2 weeks | ND | 1.1 | 97.3 | 1.6 | 35.9 | 55.5 | ND | ND |
| | 4 weeks | ND | 1.1 | 96.4 | 2.5 | 44.9 | 46.5 | ND | ND |
| | 8 weeks | ND | 1.4 | 94.5 | 4.1 | 60.4 | 33.2 | ND | ND |

*ND not determined

Formulation Q is a liquid formulation with the composition 100 mg/ml humanized 2H7, 30 mM sodium acetate, 8% trehalose dihydrate, 0.02% polysorbate 20, 0 U/ml of rhuPH20 at pH 5.3.

| Storage temperature | Storage Time | Protein concentration (mg/ml) | Size Exclusion-HPLC | | | Ion Exchange-HPLC | | CDC Potency | Enzyme |
|---|---|---|---|---|---|---|---|---|---|
| | | | HMW (%) | Monomer (%) | LMW (%) | % Acidic Variant | % Main Peak | (% Specific Activity) | activity (U/ml) |
| — | Initial | 102 | 1.0 | 98.8 | 0.2 | 27.2 | 67.5 | 101 | ND |
| 5° C. | 12 weeks | ND | 1.2 | 97.7 | 1.1 | 26.7 | 68.0 | 106 | ND |
| | 24 weeks | ND | 1.3 | 97.6 | 1.2 | 25.8 | 67.5 | 84 | ND |
| | 36 weeks | ND | 1.3 | 97.2 | 1.5 | 27.4 | 67.4 | 95 | ND |
| | 48 weeks | ND | 1.3 | 97.2 | 1.6 | 26.2 | 68.3 | 89 | ND |
| | 72 weeks | ND | 1.4 | 97.4 | 1.2 | 26.4 | 68.3 | 106 | ND |
| | 96 weeks | ND | 1.5 | 97.2 | 1.2 | 28.1 | 66.4 | 96 | ND |
| 25° C. | 4 weeks | ND | 1.2 | 97.5 | 1.2 | 31.0 | 63.7 | ND | ND |
| | 8 weeks | ND | 1.5 | 97.2 | 1.4 | 32.4 | 61.9 | ND | ND |
| | 12 weeks | ND | 1.6 | 96.7 | 1.7 | 35.4 | 58.9 | 90 | ND |
| | 24 weeks | ND | 1.9 | 96.0 | 2.1 | 40.6 | 52.1 | ND | ND |
| 40° C. | 2 weeks | ND | 1.4 | 97.1 | 1.6 | 35.4 | 57.7 | ND | ND |
| | 4 weeks | ND | 1.8 | 95.5 | 2.7 | 45.6 | 47.3 | ND | ND |
| | 8 weeks | ND | 2.3 | 93.5 | 4.3 | 60.3 | 32.9 | ND | ND |

*ND not determined

Formulation R is a liquid formulation with the composition 100 mg/ml humanized 2H7, 30 mM sodium acetate, 8% trehalose dihydrate, 0.02% polysorbate 20, 1500 U/ml of rhuPH20 at pH 5.3.

| Storage temperature | Storage Time | Protein concentration (mg/ml) | Size Exclusion-HPLC | | | Ion Exchange-HPLC | | CDC Potency | Enzyme |
|---|---|---|---|---|---|---|---|---|---|
| | | | HMW (%) | Monomer (%) | LMW (%) | % Acidic Variant | % Main Peak | (% Specific Activity) | activity (U/ml) |
| — | Initial | 101 | 1.0 | 98.8 | 0.2 | 27.3 | 67.5 | 98 | 1389 |
| 5° C. | 12 weeks | ND | 1.2 | 97.7 | 1.2 | 25.3 | 67.7 | 104 | 1655 |
| | 24 weeks | ND | 1.3 | 97.6 | 1.2 | 26.0 | 67.6 | 82 | 1381 |
| | 36 weeks | ND | 1.3 | 96.6 | 2.2 | 26.7 | 68.7 | 95 | 1644 |
| | 48 weeks | ND | 1.3 | 96.5 | 2.2 | 26.2 | 68.2 | 94 | 1381 |
| | 72 weeks | ND | 1.4 | 97.5 | 1.2 | 26.7 | 68.1 | 106 | ND |
| | 96 weeks | ND | 1.5 | 97.2 | 1.3 | 28.1 | 66.2 | 95 | ND |
| 25° C. | 4 weeks | ND | 1.2 | 97.5 | 1.2 | 29.2 | 64.2 | ND | 1376 |
| | 8 weeks | ND | 1.4 | 97.3 | 1.3 | 32.5 | 60.4 | ND | 1018 |
| | 12 weeks | ND | 1.6 | 96.9 | 1.5 | 35.3 | 58.9 | 91 | 942 |
| | 24 weeks | ND | 1.9 | 96.0 | 2.2 | 40.7 | 53.8 | ND | 616 |
| 40° C. | 2 weeks | ND | 1.3 | 97.1 | 1.5 | 35.8 | 55.8 | ND | ND |
| | 4 weeks | ND | 1.8 | 95.6 | 2.7 | 45.8 | 47.6 | ND | ND |
| | 8 weeks | ND | 2.3 | 93.6 | 4.0 | 59.3 | 32.4 | ND | ND |

*ND not determined

Formulation S is a liquid formulation with the composition 100 mg/ml humanized 2H7, 30 mM sodium acetate, 8% trehalose dihydrate, 0.02% polysorbate 20, 12,000 U/ml of rhuPH20 at pH 5.3.

| Storage temperature | Storage Time | Protein concentration (mg/ml) | Size Exclusion-HPLC | | | Ion Exchange-HPLC | | CDC Potency | Enzyme |
|---|---|---|---|---|---|---|---|---|---|
| | | | HMW (%) | Monomer (%) | LMW (%) | % Acidic Variant | % Main Peak | (% Specific Activity) | activity (U/ml) |
| — | Initial | 101 | 1.0 | 98.8 | 0.2 | 27.4 | 67.4 | 99 | 11692 |
| 5° C. | 12 weeks | ND | 1.1 | 97.6 | 1.2 | 25.8 | 68.1 | 97 | 10599 |
| | 24 weeks | ND | 1.2 | 97.6 | 1.2 | 26.1 | 67.2 | 80 | 11946 |
| | 36 weeks | ND | 1.2 | 97.1 | 1.7 | 26.1 | 69.3 | 95 | 14894 |
| | 48 weeks | ND | 1.3 | 97.0 | 1.8 | 25.7 | 68.4 | 89 | 11820 |
| | 72 weeks | ND | 1.4 | 97.4 | 1.3 | 26.4 | 68.3 | 102 | ND |
| | 96 weeks | ND | 1.5 | 97.1 | 1.4 | 28.1 | 66.2 | 97 | ND |
| 25° C. | 4 weeks | ND | 1.3 | 97.4 | 1.3 | 29.8 | 64.6 | ND | 11897 |
| | 8 weeks | ND | 1.4 | 97.1 | 1.4 | 32.5 | 61.6 | ND | 11117 |
| | 12 weeks | ND | 1.5 | 96.6 | 1.8 | 35.5 | 58.7 | 89 | 10763 |
| | 24 weeks | ND | 1.9 | 95.9 | 2.3 | 41.1 | 51.1 | ND | 7783 |

-continued

| Storage temperature | Storage Time | Protein concentration (mg/ml) | Size Exclusion-HPLC | | | Ion Exchange-HPLC | | CDC Potency (% Specific Activity) | Enzyme activity (U/ml) |
|---|---|---|---|---|---|---|---|---|---|
| | | | HMW (%) | Monomer (%) | LMW (%) | % Acidic Variant | % Main Peak | | |
| 40° C. | 2 weeks | ND | 1.4 | 97.0 | 1.6 | 35.6 | 55.9 | ND | ND |
| | 4 weeks | ND | 1.8 | 95.6 | 2.6 | 46.0 | 48.0 | ND | ND |
| | 8 weeks | ND | 2.2 | 93.8 | 4.0 | 61.4 | 32.7 | ND | ND |

*ND not determined

Example 3

Treatment of Patients with the Formulation

Rituximab-containing regimens have become the standard of care for patients suffering from various CD20-positive B-cell malignancies. Currently, rituximab is administered as an intravenous (IV) infusion over several hours. These long infusion times and the side effects related to the infusion were cited by some patients as uncomfortable consequences of the current therapeutic treatment. Furthermore, the required procedure to establish intravenous access is considered invasive and can be painful, particularly in patients with malignant diseases who are treated repeatedly. Subcutaneous (SC) administration could significantly simplify treatment, shortening administration to less than 10 minutes and improving patient experience. Recombinant human hyaluronidase (rHuPH20) has been developed and approved to improve dispersion and absorption of co-administered drugs. It has been combined with rituximab to allow injection volumes larger than 10 mL to be safely and comfortably administered SC. The aims of this treatment were to select the dose of the SC rituximab formulation with rHuPH20 prepared as described in Example 1 (Formulation A) giving comparable exposure to IV rituximab and to assess its safety and tolerability in male and female follicular lymphoma (FL) patients during maintenance treatment.

This example provides stage 1 data from a randomized, open-label, multi-centre adaptive Phase Ib study. 124 patients were randomized to one of four rituximab maintenance treatment groups: 16 patients IV control, 34 patients SC dose 1 (375 mg/m$^2$), 34 patients SC dose 2 (625 mg/m$^2$) and 40 patients SC dose 3 (800 mg/m$^2$). Prior to randomization, eligible patients were treated with at least one IV rituximab dose at 375 mg/m$^2$ in the maintenance setting. For patients randomized to one of the SC cohorts, a single IV dose was replaced by a SC dose. Patients received rituximab either on an every 2 month (q2m) or every 3 month (q3m) regimen, as per local practice. Safety data are available from a total of 119 patients. Rituximab SC was generally well tolerated. No clinically significant observations or treatment-related serious adverse events have been reported. A total of 95 adverse events (AEs) were reported in 46 patients (39%). The most commonly documented AE was "administration-associated reaction" (AAR, including rash, erythema and mild discomfort). These AARs were reversible, predominantly mild in intensity and only 1 event necessitated any treatment (metoclopramide for nausea). Overall, the AE profile is not significantly different to that expected in patients treated with rituximab IV (after AAR, the most frequent events were gastrointestinal disorders and mild infections). Four serious adverse events (SAES) were reported in 4 separate patients, all reported as unrelated to study medication. There were no AEs leading to death, withdrawal or treatment discontinuation.

The total volume administered SC in each patient ranged between 4.4-15.0 mL. The average injection duration was 2 mL/min. Rituximab maximum serum concentrations in the SC cohorts occurred between Day 2 and Day 8 (48 h and 168 h). Pharmacokinetic parameters were linear with respect to dose over the range of SC doses administered (375, 625 and 800 mg/m$^2$). Rituximab concentrations on Day 28 ($C_{28}$) and the extent of serum exposure ($AUC_{0-57}$) in patients administered 625 mg/m$^2$ rituximab SC were comparable to those in patients administered the standard rituximab IV dose of 375 mg/m$^2$ SC.

In conclusion, subcutaneous rituximab can be delivered quickly, comfortably and safely while achieving serum exposure comparable to the approved intravenous formulation in FL patients during maintenance treatment. The patient experience was favourable. These results support further testing of subcutaneous rituximab and a fixed dose of 1400 mg rituximab SC has been selected for formal $C_{trough}$ non-inferiority testing in stage 2 of the trial.

Example 4

Rituximab SQ Vs. Rituximab IV in Patients with Follicular Non-Hodgkin's Lymphoma Patients with previously untreated follicular (low grade) lymphoma are treated with maintenance treatment with either: (a) rituximab SC formulation (prepared according to Example 1, Formulation A) in combination with CHOP or CVP, or (b) rituximab IV in combination with CHOP or CVP.

Patients will be randomized to receive 375 mg/m$^2$ Rituximab as intravenous infusion or 1400 mg Rituximab given subcutaneously. In addition, patients will receive standard chemotherapy (CVP or CHOP). Patients who achieved a complete or partial response after 8 treatment cycles, will receive maintenance treatment for a further maximum number of 12 cycles. Maintenance treatment cycles will be repeated every 8 weeks. The anticipated time on study treatment is 96 weeks.

Treatment with 1400 mg SQ Rituximab anti-CD20 antibody as a maintenance treatment every 8 weeks for up to 12 cycles is expected to be safe and efficacious in treating follicular lymphoma, optionally in combination with chemotherapy (including CHOP or CVP).

The invention claimed is:
1. A highly concentrated, stable pharmaceutical formulation suitable for subcutaneous administration comprising:
   a. about 100-150 mg/ml Rituximab;
   b. a buffering agent providing a pH of 5.3- 6.5;
   c. about 15 to 250 mM saccharide as a first stabilizer;
   d. about 5 to 25 mM methionine as a second stabilizer;
   e. about 0.01 to 0.1% of a nonionic surfactant; and
   f. about 1,000 to 16,000 U/ml of recombinant human PH20 (rHuPH20) hyaluronidase enzyme.

2. A highly concentrated, stable pharmaceutical formulation according to claim 1, wherein the Rituximab concentration is 100 to 150 mg/ml.

3. A highly concentrated, stable pharmaceutical formulation according to claim 1, wherein the Rituximab concentration is 120±20 mg/ml.

4. A highly concentrated, stable pharmaceutical formulation according to claim 1, comprising about 12,000 U/ml of rHuPH20.

5. A highly concentrated, stable pharmaceutical formulation according to claim 1, wherein the buffering agent provides a pH selected from the group consisting of 5.3, 5.5, 6.0, 6.1 and 6.5.

6. A highly concentrated, stable pharmaceutical formulation according to claim 1, wherein the buffering agent is a histidine buffer.

7. A highly concentrated, stable pharmaceutical formulation according to claim 1, wherein the nonionic surfactant comprises a polysorbate.

8. A highly concentrated, stable pharmaceutical formulation according to claim 7, wherein the concentration of the polysorbate is 0.02% (w/v) to 0.08% (w/v).

9. A highly concentrated, stable pharmaceutical formulation according to claim 7, wherein the polysorbate is selected from the group consisting of polysorbate 20, polysorbate 80, and polyethylene-polypropylene copolymer.

10. A highly concentrated, stable pharmaceutical formulation according to claim 1, which is stable upon freezing and thawing.

11. A highly concentrated, stable pharmaceutical formulation according to claim 1 in liquid form.

12. A highly concentrated, stable pharmaceutical formulation according to claim 1, wherein the first stabilizer comprises trehalose.

13. A highly concentrated, stable pharmaceutical formulation according to claim 1, wherein the first stabilizer comprises sucrose.

14. A highly concentrated, stable pharmaceutical formulation suitable for subcutaneous administration comprising:
  a. about 100 to 150 mg/ml Rituximab;
  b. histidine buffer providing a pH of about 5.3 to 6.5;
  c. about 15 to 250 mM saccharide, selected from the group consisting of trehalose and sucrose, as a first stabilizer;
  d. about 5 to 25 mM methionine as a second stabilizer;
  e. about 0.02 to 0.08% of a polysorbate; and
  f. about 1,000 to 16,000 U/ml of recombinant human PH20 (rHuPH20) hyaluronidase enzyme.

15. A highly concentrated, stable, liquid pharmaceutical formulation suitable for subcutaneous administration comprising:
  a. about 120 mg/ml Rituximab;
  b. histidine buffer, pH of about 5.5;
  c. about 210 mM trehalose;
  d. about 10 mM methionine;
  e. about 0.06% polysorbate 80; and
  f. about 12,000 U/ml of recombinant human PH20 (rHuPH20) hyaluronidase enzyme.

* * * * *